(12) United States Patent
Urech et al.

(10) Patent No.: US 9,938,336 B2
(45) Date of Patent: Apr. 10, 2018

(54) SEQUENCE BASED ENGINEERING AND OPTIMIZATION OF SINGLE CHAIN ANTIBODIES

(75) Inventors: David M. Urech, Männedorf (CH); Leonardo Borras, Schlieren (CH)

(73) Assignee: Esbatech, an Alcon Biomedical Research Unit LLC, Schlieren (CH)

( * ) Notice: Subject to any disclaimer, the term of this patent is extended or adjusted under 35 U.S.C. 154(b) by 709 days.

(21) Appl. No.: 13/592,885

(22) Filed: Aug. 23, 2012

(65) Prior Publication Data

US 2013/0053259 A1    Feb. 28, 2013

Related U.S. Application Data

(63) Continuation of application No. 12/530,756, filed as application No. PCT/EP2008/001958 on Mar. 12, 2008, now Pat. No. 8,280,711.

(60) Provisional application No. 60/906,365, filed on Mar. 12, 2007.

(51) Int. Cl.
  *G06F 19/18* (2011.01)
  *C07K 16/00* (2006.01)

(52) U.S. Cl.
  CPC ........ *C07K 16/00* (2013.01); *C07K 2317/622* (2013.01); *G06F 19/18* (2013.01)

(58) Field of Classification Search
  None
  See application file for complete search history.

(56) References Cited

U.S. PATENT DOCUMENTS

| | | | |
|---|---|---|---|
| 5,714,350 A | 2/1998 | Co et al. | |
| 5,736,137 A | 4/1998 | Anderson et al. | |
| 5,824,307 A | 10/1998 | Johnson | |
| 6,258,562 B1 | 7/2001 | Salfeld et al. | |
| 6,350,861 B1 | 2/2002 | Co et al. | |
| 6,455,043 B1 | 9/2002 | Grillo-Lopez | |
| 6,602,977 B1 | 8/2003 | Ljungqvist et al. | |
| 6,673,901 B2 | 1/2004 | Koide | |
| 6,682,734 B1 | 1/2004 | Anderson et al. | |
| 6,703,199 B1 | 3/2004 | Koide | |
| 6,740,734 B1 | 5/2004 | Nilsson et al. | |
| 6,838,254 B1 | 1/2005 | Hamers et al. | |
| 6,884,879 B1 | 4/2005 | Baca et al. | |
| 7,078,490 B2 | 7/2006 | Koide | |
| 7,119,171 B2 | 10/2006 | Koide | |
| 7,258,985 B2 | 8/2007 | Maur | |
| 7,258,986 B2 | 8/2007 | Auf der Maur | |
| 7,396,917 B2 | 7/2008 | Bowdish et al. | |
| 8,280,711 B2 | 10/2012 | Urech et al. | |
| 2001/0014831 A1 | 8/2001 | Scarborough | |
| 2001/0024831 A1 | 9/2001 | Auf Der Maur et al. | |
| 2003/0096306 A1 | 5/2003 | Auf Der Maur et al. | |
| 2003/0232972 A1 | 12/2003 | Bowdish et al. | |
| 2006/0099204 A1 | 5/2006 | DoCouto | |
| 2009/0311251 A1 | 12/2009 | Auf der Maur et al. | |

FOREIGN PATENT DOCUMENTS

| | | |
|---|---|---|
| EP | 1242457 B1 | 8/2004 |
| EP | 1479694 A2 | 11/2004 |
| EP | 0519596 B1 | 2/2005 |
| WO | 1999016873 | 4/1999 |
| WO | 2000063243 | 10/2000 |
| WO | 20010048017 A1 | 7/2001 |
| WO | 2001064942 A1 | 9/2001 |
| WO | 0185797 A1 | 11/2001 |
| WO | 2002020565 A2 | 3/2002 |
| WO | 2002088171 A2 | 11/2002 |
| WO | 20030008451 A2 | 1/2003 |
| WO | 2004044011 A2 | 5/2004 |
| WO | 2005005604 A2 | 1/2005 |
| WO | 2005019254 A1 | 3/2005 |
| WO | 2005051998 A2 | 6/2005 |
| WO | 2006013468 A2 | 2/2006 |
| WO | 2006040153 | 4/2006 |
| WO | 2006083275 A2 | 8/2006 |
| WO | 2006131013 A2 | 12/2006 |
| WO | 2007070750 A1 | 6/2007 |
| WO | 2008006235 A2 | 1/2008 |

(Continued)

OTHER PUBLICATIONS

Lehmann et al. Engineering proteins for thermostability: the use of sequence alignments versus rational design and directed evolution Current Opinion in Biotechnology vol. 12, pp. 371-375 (2001).*
Marvin et al. Redesigning an Antibody Fragment for Faster Association with Its Antigen Biochemistry vol. 42, pp. 7077-7083 (2003).*
Ohage et al. Beta-Turn propensities as paradigms for the analysis of structural motifs to engineer protein stability Protein Science vol. 6, pp. 233-241 (1997).*
Hudson Recombinant antibody fragments Current Opinion in Biotechnology vol. 9, pp. 395-402 (1998).*
Ramirez-Benitez et al. VIR.II: a new interface with the antibody sequences in the Kabat database BioSystems vol. 61, pp. 125-131 (2001).*

(Continued)

*Primary Examiner* — John S. Brusca
(74) *Attorney, Agent, or Firm* — Jason J. Derry

(57) ABSTRACT

The invention provides methods of using sequence based analysis and rational strategies to modify and improve the structural and biophysical properties of single chain antibodies (scFvs), including stability, solubility, and antigen binding affinity. These methods and strategies can be used individually or in combination. The methods of the present invention also include the use of a database comprising scFv sequences from an experimentally screened scFv library of antibodies that have been selected to have superior solubility and stability. The invention also provides methods of using the properties found for these selected antibodies in a general approach for reshaping scFv antibodies to improve stability and solubility properties of a single chain antibody fragment.

2 Claims, 8 Drawing Sheets

(56) References Cited

FOREIGN PATENT DOCUMENTS

| | | |
|---|---|---|
| WO | 2008110348 A1 | 9/2008 |
| WO | 2009000098 A2 | 12/2008 |
| WO | 2009000099 A2 | 12/2008 |

OTHER PUBLICATIONS

Wirtz et al. Intrabody construction and expression III: Engineering hyperstable Vh domains Protein Science vol. 8, pp. 2245-2250 (1999).*
Studnicka GM, et al., "Human-engineered monoclonal antibodies retain full specific binding activity by preserving non-CDR complementarity-modulating residues," Protein Eng. (1994); pp. 805-814; vol. 7, No. 6.
De Haard, et al., "Absolute conservation of residue 6 of immunoglobulin heavy chain variable regions of class IIA is required for correct folding," Protein Eng. (1998); pp. 1267-1276; vol. 11, No. 12.
Sheikholvaezin A. et al., Optimizing the generation of recombinant single-chain antibodies against placental alkaline phosphatase. Hybridoma (Larchmt). Aug. 2006; 25(4): 181-92.
Arakawa et al.; "Cloning and sequencing of the VH and Vx genes of an anti-CD3 monoclonal antibody, and construction of a mouse/human chimeric antibody"; J. Biochem; vol. 120; pp. 657-662 (1996).
Carter; "Potent antibody therapeutics by design"; Focus on Translational Immunology; Nature Publishing; vol. 6; pp. 343-357 (May 2006).
Chowdhury et al.; Improved stability and yield of a Fv-toxin fusion protein by computer design and protein engineering of the Fv; Journal of Molecular Biology; vol. 281; pp. 917-928 (198).
Chowdhury and Vasmatzis; "Engineering scFvs for improved stability"; Methods in Molecular Biology; vol. 27; pp. 237-254.
Dumoulin et al.; "Single-domain antibody fragments with high conformational stability"; Protein Science; vol. 11; pp. 500-515 (2002).
Ewert et al.; "Stability improvement of antibodies for extracellular and intracellular applications: CDR grafting to stable frameworks and structure-based framework engineering"; Methods; vol. 34; pp. 184-199 (2004).
Filpula; "Antibody engineering and modification technologies"; Biomolecular Engineering; vol. 24; pp. 201-215 (2007).
Hamers-Casterman et al.; "Naturally occurring antibodies devoid of light chains"; Letters to Nature; Nature; vol. 363; pp. 446-448 (Jun. 3, 1993).
Hoet et al; "Generation of high-affinity human antibodies by combining donor-derived and synthetic complementary-determining-region diversity; Nature" Biotechnology; Nature Publishing; vol. 23; No. 3; pp. 344-348 (Mar. 1, 2005).
Johnson et al; "The kabat database and a bioinformatics example"; Methods in Molecular Biology; Antibody Engineering; Methods and Protocols; vol. 248; pp. 11-25.
Jung et al; "The importance of framework residues H6, H7 and H10 in antibody heavy chains: experimental evidence for a new structural subclassification of antibody VH domains"; Journal of Molecular Biology; vol. 309; pp. 701-716 (2001).
Kung et al.; "Monoclonal antibodies defining distinctive human T cell surface antigens"; Science; vol. 206; pp. 347-349 (Oct. 19, 1979).
Reinherz et al.; "Monoclonal antibodies defining distinctive human T cell surface antigens"; Science: vol. 206; pp. 347-349 (Oct. 19, 1979).
Zahnd et al; Directed in vitro evolution and crystallographic analysis of a peptide-binding single chain antibody fragment (scFv) with low picomolar affinity; Journal of Biological Chemistry; vol. 279; No. 18; pp. 18870-18877 (Apr. 30, 2004).
Deret et al., "SUBIM: a program for analyzing the Kabat database and determining the variability subgroup of a new immunoglobulin sequence", Oxford University Press; vol. 11; No. 4; pp. 435-439 (1995).

Ewert et al.; "Structure based improvement of the biophysical properties of immunoglobulin VH domains with a generalizable approach"; Biochemistry; vol. 42; pp. 1517-1528 (2003).
Honegger et al.; "Yet another numbering scheme for immunoglobulin variable domains: an automatic modeling and analysis tool"; J. Mol. Biol.; vol. 309; pp. 657-670 (2001).
Johnson et al.; "The Kabat database and a bioinformatics example"; Methods in Molecular Biology; vol. 268; pp. 11-25 (2004).
Knappik et al.; "Fully synthetic human combinatorial antibody libraries (HuCAL) based on modular consensus frameworks and CDRs randomized with trinucleotides"; J. Mol. Biol.; vol. 296; pp. 57-86 (2000).
Monsellier et al.; "Improving the stability of an antibody variable fragment by a combination of knowledge-based approaches: Validation and Mechanisms"; J. Mol. Biol.; vol. 362; pp. 580-593 (2006).
Pommie et al.; IMGT standardized criteria for statistical analysis of immunoglobulin V-REGION amino acid properties; J. Mol. Recognit.; vol. 17; pp. 17-32 (2004).
Worn et al.; "Stability engineering of antibody single-chain Fv fragments"; J. Mol. Biol.; vol. 305; pp. 989-1010 (2001).
McCarthy et al.; "Altering the fine specificity of an anti-legionella single chain antibody by a single amino acid insertion"; J. Immun. Methods; vol. 251; pp. 137-149 (2001).
Nieba et al.; "Disrupting the hydrophobic patches at the antibody variable/constant domain interface: improved in vivo folding and physical characterization of an engineered scFv fragment"; Protein Engineering; vol. 10; pp. 435-444 (1997).
Search Report, Written Opinion and IPR corresponding to PCT Application Serial No. PCT EP2008/001958.
Auf Der Maur, et al. "Antigen-independent selection of intracellular stable antibody frameworks"; Methods; vol. 34; pp. 215-224 (2004).
Barberis et al.; "Contact with a component of the polymerase II holoenzyme suffices for gene activation"; Cell; vol. 81; pp. 359-368 (May 5, 1995).
Berge et al.; "Review Article: Pharmaceutical Salts"; Journal of Pharmaceutical Sciences; vol. 66; No. 1; pp. 1-19 (Jan. 1977).
Bird et al.; "Single-chain antigen-binding proteins"; Science; vol. 242; pp. 423-426 (Oct. 21, 1988).
Choulier et al.; "Covariance analysis of protein families:the case of the variable domains of antibodies"; Proteins: Structure, Function, and Genetics; vol. 41; pp. 475-484 (2000).
Cox et al.; "A directory of human germ-line Vx segments reveals a strong bias in their usage"; Eur. J. Immunol.; vol. 24; pp. 827-236 (1994).
Demarest et al.; "Optimization of the antibody CH3 domain by residue frequency analysis of IgG sequences"; J. Mol. Biol.; vol. 335; pp. 41-48 (2004).
Ewert et al.; "Structure-based improvement of the biophysical properties of immunoglobulin VH domains with a generalizable approach"; Biochemistry; vol. 42; pp. 1517-1528 (2003).
Huston et al.; "Protein engineering of antibody binding sites: recovery of specific activity in an anti-digoxin single-chain Fv analogue produced in *Escherichia coli*"; Proc. Natl. Acad. Sci.; vol. 85; pp. 5879-5883 (Aug. 1988).
Johnson and Wu; "Kabat database and its applications: 30 years after the first variability plot"; Nucleic Acids Research; vol. 28; No. 1; pp. 214-218 (2000).
Johnson and Wu; "Kabat database and its applications: future directions"; Nucleic Acids Research; vol. 29; No. 1; pp. 205-206 (2001).
Jung et al.; "Selection for improved protein stability by phage display"; J. Mol. Biol.; vol. 294; pp. 163-180 (1999).
Jung and Pluckthun; "Improving in vivo folding and stability of a single-chain Fv antibody fragment by loop grafting"; Protein Engineering; vol. 10; No. 8; pp. 959-966 (1997).
Larson Adn Davidson; "The identification of conserved interactions within the SH3 domain by alignment of sequences and structures"; Protein Science; vol. 9; pp. 2170-2180 (2000).
Lefranc et al.; "IMGT, the international immunogene tics database"; Nucleic Acids Research; vol. 27; No. 1; pp. 209-212 (1999).

(56) References Cited

OTHER PUBLICATIONS

Lefranc; "IMGT, the international immunogene tics database"; Nucleic Acids Research; vol. 29; No. 1; pp. 207-209 (2001).
Lefranc; "IMGT, the international immunogene tics database"; Nucleic Acids Research; vol. 31; No. 1; pp. 307-310 (2003).
Needleman and Wunsch; "A general method applicable to the search for similarities in the amino acid sequence of two proteins"; J. Mol. Biol.; vol. 48; pp. 443-453 (1970).
Ohage and Steipe; "Intrabody construction and expression. I. The critical role of VL domain stability"; J. Mol. Biol.; vol. 291; pp. 1119-1128 (1999).
Ruiz et al.; "IMGT, the international immunogene tics database"; Nucleic Acids Research; vol. 28; No. 1; pp. 219-221 (2000).
Schier et al.; "Isolation of high-affinity monomeric human anti-c-erbB-2 single chain Fv using affinity-driven selection"; J. Mol. Biol.; vol. 255; pp. 28-43 (1996).
Shenkin et al.; "Information-theoretical entropy as a measure of sequence variability"; Proteins: Structure, Function and Genetics; vol. 11; pp. 297-313 (1991).
Skerra and Pluckthun; "Assembly of a functional immunoglobulin Fv fragment in *Escherichia coli*"; Science; vol. 240; pp. 1038-1041 (May 20, 1988).
Steipe et al.; "Sequence statistics reliability predict stabilizing mutations in a protein domain"; J. Mol. Biol.; vol. 240; pp. 188-192 (1994).
Tan et al.; "Contributions of a highly conserved VH/VL hydrogen bonding interaction to scFv folding stability and refolding efficiency"; Biophysical Journal; vol. 75; pp. 1473-1482 (Sep. 1998).
Tomlinson et al.; "The repertoire of human germline VH sequences reveals about fifty groups of VH segments with different hypervariable loops"; J. Mol. Biol.; vol. 227; pp. 776-798 (1992).
Ward et al.; "Binding activities of a repertoire of single immunoglobulin variable domains secreted from *Escherichia coli*"; Letters to Nature; Nature; vol. 341; pp. 554-546 (Oct. 12, 1989).
Williams and Winter; "Cloning and sequencing of human immunoglobulin Vx gene segments"; Eur. J. Immunol.; vol. 23; pp. 1456-1461 (1993).
Worn and Pluckthun; "Mutual stabilization of VL and VH in single-chain antibody fragments, investigated with mutants engineered for stability"; Biochemistry; vol. 37; pp. 13120-13127 (1998).
Worn and Pluckthun; "Different equilibrium stability behavior of ScFv fragments: Identification, classification, and improvement by protein engineering"; vol. 38; pp. 8739-8750 (1999).
Wu et al.; "Humanization of a murine monoclonal antibody by simultaneous optimization of framework and CDR residues"; J. Mol. Biol.; vol. 294; pp. 151-162 (1999).
Zhang M. et al., "Rheumatoid factor specificity of a VH3-encoded antibody is dependent on the heavy chain CDR3 region and is independent of a protein binding," Journal of Immunology (1998); pp. 2284-2285; vol. 161, No. 5.

* cited by examiner

A

B

US 9,938,336 B2

SEQUENCE BASED ENGINEERING AND OPTIMIZATION OF SINGLE CHAIN ANTIBODIES

RELATED APPLICATIONS

The present application is a continuation of U.S. patent application Ser. No. 12/530,756 filed Oct. 9, 2009, which claims benefit to a 371 Patent Application Serial No. PCT/EP2008/001958 filed Mar. 12, 2008, which claims priority to U.S. Provisional Application Ser. No. 60/906,365, entitled "Sequence Based Engineering and Optimization of Single Chain Antibodies", filed on Mar. 12, 2007.

The entire contents of the aforementioned applications are hereby incorporated herein by reference.

BACKGROUND OF THE INVENTION

Antibodies have proven to be very effective and successful therapeutic agents in the treatment of cancer, autoimmune diseases and other disorders. While full-length antibodies typically have been used clinically, there are a number of advantages that use of an antibody fragment can provide, such as increased tissue penetration, absence of Fc-effector function combined with the ability to add other effector functions and the likelihood of less systemic side effects resulting from a shorter in vivo half life systemically. The pharmacokinetic properties of antibody fragments indicate that they may be particularly well suited for local therapeutic approaches. Furthermore, antibody fragments can be easier to produce than full-length antibodies in certain expression systems.

One type of antibody fragment is a single chain antibody (scFv), which is composed of a heavy chain variable domain ($V_H$) conjugated to a light chain variable domain ($V_L$) via a linker sequence. Thus, scFvs lack all antibody constant region domains and the amino acid residues of the former variable/constant domain interface (interfacial residues) become solvent exposed. A scFv can be prepared from a full-length antibody (e.g., IgG molecule) through established recombinant engineering techniques. The transformation of a full length antibody into a scFv, however, often results in poor stability and solubility of the protein, low production yields and a high tendency to aggregate, which raises the risk of immunogenicity.

Accordingly, attempts have been made to improve properties such as solubility and stability of scFvs. For example, Nieba, L. et al. (Prot. Eng. (1997) 10:435-444) selected three amino acid residues known to be interfacial residues and mutated them. They observed increased periplasmic expression of the mutated scFv in bacteria, as well as a decreased rate of thermally induced aggregation, although thermodynamic stability and solubility were not significantly altered. Other studies in which site directed mutagenesis was carried out on particular amino acid residues within the scFv also have been reported (see e.g., Tan, P. H. et al. (1988) *Biophys. J.* 75:1473-1482; Worn, A. and Pluckthun, A. (1998) *Biochem.* 37:13120-13127; Worn, A. and Pluckthun, A. (1999) *Biochem.* 38:8739-8750). In these various studies, the amino acid residues selected for mutagenesis were chosen based on their known positions within the scFv structure (e.g., from molecular modeling studies).

In another approach, the complementarity determining regions (CDRs) from a very poorly expressed scFv were grafted into the framework regions of a scFv that had been demonstrated to have favorable properties (Jung, S. and Pluckthun, A. (1997) *Prot. Eng.* 10:959-966). The resultant scFv showed improved soluble expression and thermodynamic stability.

Progress in the engineering of scFvs to improve functional properties is reviewed in, for example, Worn, A. and Pluckthun, A. (2001) *J. Mol. Biol.* 305:989-1010. New approaches, however, are still needed that allow for rational design of scFvs with superior functional properties, in particular approaches that assist the skilled artisan in selection of potentially problematic amino acid residues for engineering.

SUMMARY OF THE INVENTION

This invention provides methods that allow for the identification of potentially problematic amino acid residues within a scFv sequence using sequence based analyses. Furthermore, amino acid residues identified in accordance with the methods of the invention can be selected for mutation and engineered scFvs that have been mutated can be prepared and screened for improved functional properties. In a particularly preferred embodiment, the invention provides methods in which a database of functionally-selected scFvs is used to identify amino acid residue positions that are either more or less tolerant of variability than the corresponding positions in germline and/or mature antibody immunoglobulin sequences, thereby indicating that such identified residue positions may be suitable for engineering to improve scFv functionality such as stability and/or solubility. Thus, the invention provides, and demonstrates the benefit of, a "functional consensus" approach based on the use of a database of functionally-selected scFv sequences.

In yet other preferred embodiments, the invention provides methods for identifying preferred amino acid residues to be substituted (or alternatively, amino acid residues to be excluded) at amino acid positions of interest (e.g., amino acid positions identified by comparing a database of scFv sequences having at least one desirable property, e.g., as selected with QC assay, versus a database of mature antibody sequences, e.g., the Kabat database) in an immunobinder. Thus the invention further provides "enrichment/exclusion" methods for selecting a particular amino acid residue. Still further, the invention provides methods of engineering immunobinders (e.g., scFvs) by mutating particular framework amino acid positions identified using the "functional consensus" approach described herein. In preferred embodiments, the framework amino acid positions are mutated by substituting the existing amino acid residue by a residue which is found to be an "enriched" residue using the "enrichment/exclusion" analysis methods described herein.

In one aspect, the invention provides a method of identifying an amino acid position for mutation in a single chain antibody (scFv), the scFv having $V_H$ and $V_L$ amino acid sequences, the method comprising:

a) entering the scFv $V_H$, $V_L$ or $V_H$ and $V_L$ amino acid sequences into a database that comprises a multiplicity of antibody $V_H$, $V_L$ or $V_H$ and $V_L$ amino acid sequences such that the scFv $V_H$, $V_L$ or $V_H$ and $V_L$ amino acid sequences are aligned with the antibody $V_H$, $V_L$ or $V_H$ and $V_L$ amino acid sequences of the database;

b) comparing an amino acid position within the scFv $V_H$ or $V_L$ amino acid sequence with a corresponding position within the antibody $V_H$ or $V_L$ amino acid sequences of the database;

c) determining whether the amino acid position within the scFv $V_H$ or $V_L$ amino acid sequence is occupied by an amino acid residue that is conserved at the corresponding position within the antibody $V_H$ or $V_L$ amino acid sequences of the database; and d) identifying the amino acid position within the scFv $V_H$ or $V_L$ amino acid sequence as an amino acid position for mutation when the amino acid position is occupied by an amino acid residue that is not conserved at the corresponding position within the antibody $V_H$ or $V_L$ amino acid sequences of the database.

The method can further comprise mutating the amino acid position identified for mutation within the scFv $V_H$ or $V_L$ amino acid sequence. For example, the amino acid position identified for mutation can be substituted with an amino acid residue that is conserved at the corresponding position within the antibody $V_H$ or $V_L$ amino acid sequences of the database. Additionally or alternatively, the amino acid position identified for mutation can be mutated by random mutagenesis or by biased mutagenesis to generate a library of mutated scFvs, followed by screening of the library of mutated scFvs and selection of scFvs having at least one improved functional property (e.g., by screening of the library using a yeast Quality Control-system (QC-system)).

Various types of databases can be used in the methods of the invention. For example, in one embodiment, the antibody $V_H$, $V_L$ or $V_H$ and $V_L$ amino acid sequences of the database are germline antibody $V_H$, $V_L$ or $V_H$ and $V_L$ amino acid sequences. In another embodiment, the antibody $V_H$, $V_L$ or $V_H$ and $V_L$ amino acid sequences of the database are rearranged, affinity matured antibody $V_H$, $V_L$ or $V_H$ and $V_L$ amino acid sequences. In yet another, particularly preferred, embodiment, the antibody $V_H$, $V_L$ or $V_H$ and $V_L$ amino acid sequences of the database are scFv antibody $V_H$, $V_L$ or $V_H$ and $V_L$ amino acid sequences selected as having at least one desirable functional property (such as scFv stability or scFv solubility). In yet another embodiment, more than one database can be used for comparison purposes. For example, in a particularly preferred embodiment, a database of scFvs selected as having at least one desirable functional property is used, as well as one or more germline databases or rearranged, affinity-matured antibody databases, wherein the sequence comparison results from the scFv database are compared to the results from the other database(s).

The methods of the invention can be used to analyze, for example, the $V_H$ region of a scFv, the $V_L$ region of a scFv or both. Thus, in one embodiment, the scFv $V_H$ amino acid sequence is entered into the database and aligned with antibody $V_H$ amino acid sequences of the database. In another embodiment, the scFv $V_L$ amino acid sequence is entered into the database and aligned with antibody $V_L$ amino acid sequences of the database. In yet another embodiment, the scFv $V_H$ and $V_L$ amino acid sequences are entered into the database and aligned with antibody $V_H$ and $V_L$ amino acid sequences of the database.

While the methods of the invention can be used to analyze a single amino acid position of interest within a scFv of interest, more preferably the methods are used to analyze multiple amino acid positions along the scFv sequence. Thus, in a preferred embodiment, in step b) of the method, multiple amino acid positions within the scFv $V_H$ or $V_L$ amino acid sequence are compared with corresponding positions within the antibody $V_H$ or $V_L$ amino acid sequences of the database. For example, in a preferred embodiment, each framework position within the scFv $V_H$, $V_L$ or $V_H$ and $V_L$ amino acid sequences is compared with each corresponding framework position within the antibody $V_H$, $V_L$ or $V_H$ and $V_L$ amino acid sequences of the database. Additionally or alternatively, one or more positions within one or more CDRs of the scFv can be analyzed. In yet another embodiment, each amino acid position within the scFv $V_H$, $V_L$ or $V_H$ and $V_L$ amino acid sequences is compared with each corresponding amino acid position within the antibody $V_H$, $V_L$ or $V_H$ and $V_L$ amino acid sequences of the database.

An amino acid position that is "conserved" among the sequences of the database may be occupied by one or more particular types of amino acid residues. For example, in one embodiment, the "conserved" position is occupied by one particular amino acid residue that occurs at a very high frequency at that position. That is, in step c) of the method, the amino acid residue that is conserved at the corresponding position within the antibody $V_H$ or $V_L$ amino acid sequences of the database is the amino acid residue that is most frequently at that position within the antibody $V_H$ or $V_L$ amino acid sequences of the database. In this situation, to create an engineered scFv, the amino acid position identified for mutation can be substituted with the amino acid residue that is most frequently at the corresponding position within the antibody $V_H$ or $V_L$ amino acid sequences of the database.

In another embodiment, an amino acid position that is "conserved" among the sequences of the database can be occupied by, for example, (i) hydrophobic amino acid residues, (ii) hydrophilic amino acid residues, (iii) amino acid residues capable of forming a hydrogen bond or (iv) amino acid residues having a propensity to form a β-sheet. That is, in step c) of the method, the corresponding position within the antibody $V_H$ or $V_L$ amino acid sequences of the database is conserved with: (i) hydrophobic amino acid residues, (ii) hydrophilic amino acid residues, (iii) amino acid residues capable of forming a hydrogen bond or (iv) amino acid residues having a propensity to form a β-sheet.

Accordingly, to create an engineered scFv, when the corresponding position within the antibody $V_H$ or $V_L$ amino acid sequences of the database is conserved with hydrophobic amino acid residues, the amino acid position identified for mutation within the scFv can be substituted with a hydrophobic amino acid residue that is most frequently at the corresponding position within the antibody $V_H$ or $V_L$ amino acid sequences of the database. Additionally or alternatively, the amino acid position identified for mutation within the scFv can be substituted with a hydrophobic amino acid residue that is selected as being the best fit at that position within the scFv (e.g., the hydrophobic residue most likely to maintain the structure and function of the scFv based on molecular modeling studies). Additionally or alternatively, the amino acid position identified for mutation within the scFv can be substituted with a panel of hydrophobic amino acid residues via site directed mutagenesis to create a library of engineered scFvs and the most preferred substitution(s) can be selected by screening of the library for desirable functional properties (e.g., in a yeast QC-System).

Furthermore, to create an engineered scFv, when the corresponding position within the antibody $V_H$ or $V_L$ amino acid sequences of the database is conserved with hydrophilic amino acid residues, the amino acid position identified for mutation within the scFv can be substituted with a hydrophilic amino acid residue that is most frequently at the corresponding position within the antibody $V_H$ or $V_L$ amino acid sequences of the database. Additionally or alternatively, the amino acid position identified for mutation within the scFv can be substituted with a hydrophilic amino acid residue that is selected as being the best fit at that position within the scFv (e.g., the hydrophilic residue most likely to maintain the structure and function of the scFv based on molecular modeling studies). Additionally or alternatively, the amino acid position identified for mutation within the scFv can be substituted with a panel of hydrophilic amino acid residues via site directed mutagenesis to create a library of engineered scFvs and the most preferred substitution(s) can be selected by screening of the library for desirable functional properties (e.g., in a yeast QC-System).

Still further, to create an engineered scFv, when the corresponding position within the antibody $V_H$ or $V_L$ amino acid sequences of the database is conserved with amino acid residues capable of forming a hydrogen bond, the amino acid position identified for mutation within the scFv can be substituted with the amino acid residue capable of forming a hydrogen bond that is most frequently at the corresponding position within the antibody $V_H$ or $V_L$ amino acid sequences of the database. Additionally or alternatively, the amino acid position identified for mutation within the scFv can be substituted with an amino acid residue capable of forming a hydrogen bond that is selected as being the best fit at that position within the scFv (e.g., the residue most likely to maintain the structure and function of the scFv based on molecular modeling studies). Additionally or alternatively, the amino acid position identified for mutation within the scFv can be substituted with a panel of amino acid residues capable of forming a hydrogen bond, via site directed mutagenesis, to create a library of engineered scFvs and the most preferred substitution(s) can be selected by screening of the library for desirable functional properties (e.g., in a yeast QC-System).

Still further, to create an engineered scFv, when the corresponding position within the antibody $V_H$ or $V_L$ amino acid sequences of the database is conserved with amino acid residues having a propensity to form a β-sheet, the amino acid position identified for mutation within the scFv can be substituted with the amino acid residue having a propensity to form a β-sheet that is most frequently at the corresponding position within the antibody $V_H$ or $V_L$ amino acid sequences of the database. Additionally or alternatively, the amino acid position identified for mutation within the scFv can be substituted with an amino acid residue having a propensity to form a β-sheet that is selected as being the best fit at that position within the scFv (e.g., the residue most likely to maintain the structure and function of the scFv based on molecular modeling studies). Additionally or alternatively, the amino acid position identified for mutation within the scFv can be substituted with a panel of amino acid residues having a propensity to form a β-sheet, via site directed mutagenesis, to create a library of engineered scFvs and the most preferred substitution(s) can be selected by screening of the library for desirable functional properties (e.g., in a yeast QC-System).

In another embodiment, the method of the invention for identifying an amino acid position for mutation in a scFv can be performed using a database that is a constrained database in which only those antibody $V_H$, $V_L$ or $V_H$ and $V_L$ amino acid sequences having high similarity to the scFv antibody $V_H$, $V_L$ or $V_H$ and $V_L$ amino acid sequences are included in the database.

In a preferred embodiment, to quantitate the conservation of the amino acid position being analyzed (i.e., the "corresponding position" within the antibody $V_H$ or $V_L$ amino acid sequence of the database), the amino acid position is assigned a degree of conservation using Simpson's Index.

The methods of the invention also can be used to examine pairs of amino acid positions within the scFv sequence, to identify amino acid positions that covary with each other such that one or both of these covariant pair positions can be identified for mutation. Thus, in another embodiment, the invention provides a method comprising:

a) carrying out a covariance analysis on antibody $V_H$ or $V_L$ amino acid sequences of a database to identify a covariant pair of amino acid positions;

b) comparing the covariant pair of amino acid positions with corresponding positions within a scFv $V_H$ or $V_L$ amino acid sequence;

c) determining whether the corresponding positions within the scFv $V_H$ or $V_L$ amino acid sequence are occupied by amino acid residues that are conserved at the covariant pair of amino acid positions within the antibody $V_H$ or $V_L$ amino acid sequences of the database; and d) identifying one or both of the corresponding positions within the scFv $V_H$ or $V_L$ amino acid sequence as an amino acid position for mutation when one or both of the corresponding positions within the scFv is occupied by an amino acid residue that is not conserved at the covariant pair of amino acid positions within the antibody $V_H$ or $V_L$ amino acid sequences of the database.

This covariance analysis also can be combined with the analysis of individual amino acid positions such that the method described above with steps a)-d) can further comprise the steps:

e) carrying out a covariance analysis on the antibody $V_H$ or $V_L$ amino acid sequences of the database to identify a covariant pair of amino acid positions;

f) comparing the covariant pair of amino acid positions with corresponding positions within the scFv $V_H$ or $V_L$ amino acid sequence;

g) determining whether the corresponding positions within the scFv $V_H$ or $V_L$ amino acid sequence are occupied by amino acid residues that are conserved at the covariant pair of amino acid positions within the antibody $V_H$ or $V_L$ amino acid sequences of the database; and h) identifying one or both of the corresponding positions within the scFv $V_H$ or $V_L$ amino acid sequence as an amino acid position for mutation when one or both of the corresponding positions within the scFv is occupied by an amino acid residue that is not conserved at the covariant pair of amino acid positions within the antibody $V_H$ or $V_L$ amino acid sequences of the database.

The covariance analysis methods can be applied to a single covariant pair or, alternatively, multiple covariant pairs of amino acid positions can be identified within the antibody $V_H$ or $V_L$ amino acid sequence of the database and compared to the corresponding positions within the scFv $V_H$ or $V_L$ amino acid sequence.

The method can further comprise mutating one or both of the corresponding positions within the scFv that are occupied by an amino acid residue that is not conserved at the covariant pair of amino acid positions within the antibody $V_H$ or $V_L$ amino acid sequences of the database. For example, in one embodiment, one of the corresponding positions within the scFv that is occupied by an amino acid residue that is not conserved at the covariant pair of amino acid positions is substituted with an amino acid residue that is most frequently at the covariant pair amino acid position. In another embodiment, both of the corresponding positions within the scFv that are occupied by amino acid residues that are not conserved at the covariant pair of amino acid positions are substituted with amino acid residues that are most frequently at the covariant pair amino acid positions.

The sequence-based methods of the invention for identifying amino acid positions for mutation with a scFv sequence can be combined with other methods that allow for structural analysis of scFvs. For example, in one embodiment, the sequence-based methods can be combined with molecular modeling methods to further analyze the structure of the scFv. Thus, in one embodiment, the methods described above with steps a)-d) can further comprise, for example, the steps of:

e) subjecting the scFv $V_H$, $V_L$ or $V_H$ and $V_L$ amino acid sequences to molecular modeling; and f) identifying at least one additional amino acid position within the scFv $V_H$, $V_L$ or $V_H$ and $V_L$ amino acid sequences for mutation.

This method can further comprise mutating the at least one additional amino acid position within scFv $V_H$, $V_L$ or $V_H$ and $V_L$ amino acid sequences identified for mutation by molecular modeling.

In another aspect, the invention pertains to scFv compositions prepared according to the methods of the invention in which one or more mutations are made at one or more amino acid positions identified for mutation. Pharmaceutical formulations are also provided, which formulations typically comprise the scFv composition and a pharmaceutically acceptable carrier.

In yet another aspect, the invention provides a method of identifying one or more framework amino acid positions for mutation in a single chain antibody (scFv), the scFv having $V_H$ and $V_L$ amino acid sequences, the method comprising:

a) providing a first database of $V_H$, $V_L$ or $V_H$ and $V_L$ amino acid sequences;

b) providing a second database of scFv antibody $V_H$, $V_L$ or $V_H$ and $V_L$ amino acid sequences selected as having at least one desirable functional property;

c) determining amino acid variability at each framework position of the first database and at each framework position of the second database;

d) identifying one or more framework positions at which degree of amino acid variability differs between the first database and the second database to thereby identify one or more framework amino acid positions for mutation in a single chain antibody (scFv).

Preferably, the amino acid variability at each framework position is determined by assigning a degree of conservation using Simpson's Index. In one embodiment, the one or more framework amino acid positions is identified for mutation based on the one or more framework amino acid positions having a lower Simpson's Index (SI) value in the second database as compared to the first database. In another embodiment, the one or more framework amino acid positions is identified for mutation based on the one or more framework amino acid positions having a higher Simpson's Index value in the second database as compared to the first database (e.g., germline database). In one preferred embodiment, the amino acid position of the second database (e.g., a QC database) has a SI value that is at least 0.01 less, and more preferably 0.05 less (e.g., 0.06, 0.07, 0.08, 0.09, or 0.1), than the SI value of the corresponding amino acid position in the first database (e.g., a Kabat database). In more preferred embodiments, the amino acid position of the second database has a SI value that is at least 0.1 less (e.g., 0.1, 0.15, 0.2, 0.25, 0.3, 0.35, 0.4, 0.45, or 0.5 less) than the SI value of the corresponding amino acid position in the first database.

In another aspect, the invention provides a method of identifying a preferred amino acid residue for substitution in an immunobinder, the method comprising:

a) providing a first database of grouped $V_H$ or $V_L$ amino acid sequences (e.g., germline and/or mature antibody sequences grouped according to Kabat family subtype);

b) providing a second database of grouped scFv antibody $V_H$ or $V_L$ amino acid sequences selected as having at least one desirable functional property (e.g., according to a QC assay);

c) determining amino acid frequency for an amino acid residue at a framework position of the first database and at a corresponding framework position of the second database;

d) identifying the amino acid residue as a preferred amino acid residue for substitution at a corresponding amino acid position of the immunobinder when the amino acid residue occurs at a higher frequency in the second database relative to the first database (i.e., an enriched residue).

In certain embodiments, the amino acid residue in step (d) is identified if the ratio of the relative frequency of the amino acid residue between the first and second databases (herein, the "enrichment factor") is at least 1 (e.g., 1, 2, 3, 4, 5, 6, 7, 8, 9 or 10). In a preferred embodiment, the enrichment factor is greater than about 1.0 (e.g. 1.0, 1.1, 1.2, 1.3, 1.4 or 1.5). In yet another preferred embodiment, the enrichment factor is about 4.0 to about 6.0 (e.g., 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9 or 6.0). In another embodiment, the enrichment factor is about 6.0 to about 8.0 (e.g., 6.0, 6.1, 6.2, 6.3, 6.4, 6.5, 6.6, 6.7, 6.8, 6.9, 7.0, 7.1, 7.3, 7.4, 7.5, 7.6, 7.7, 7.8, 7.9 or 8.0).

In yet another aspect, the invention provides a method of identifying an amino acid residue to be excluded from an immunobinder, the method comprising:

a) providing a first database of grouped $V_H$ or $V_L$ amino acid sequences (e.g., germline and/or mature antibody sequences grouped according to Kabat family subtype);

b) providing a second database of grouped scFv antibody $V_H$ or $V_L$ amino acid sequences selected as having at least one desirable functional property (e.g., according to a QC assay);

c) determining amino acid frequency for an amino acid residue at a framework position of the first database and at a corresponding framework position of the second database;

d) identifying the amino acid residue as a disfavored amino acid residue for substitution at a corresponding amino acid position of the immunobinder when the amino acid residue occurs at a lower frequency in the second database relative to the first database, wherein said amino acid residue type is a disfavored amino acid residue (i.e., an excluded residue). In certain preferred embodiments, the disfavored amino acid residue is identified if the enrichment factor (EF) is less than 1.

In certain embodiments, the first database comprises germline $V_H$, $V_L$ or $V_H$ and $V_L$ amino acid sequences. In other embodiments, the first database consists of germline $V_H$, $V_L$ or $V_H$ and $V_L$ amino acid sequences. In yet another embodiment, the first database comprises mature $V_H$, $V_L$ or $V_H$ and $V_L$ amino acid sequences. In another embodiment, the first database consists of mature $V_H$, $V_L$ or $V_H$ and $V_L$ amino acid sequences. In an exemplary embodiment, the mature $V_H$, $V_L$ or $V_H$ and $V_L$ amino acid sequences are from a Kabat database (KDB).

In certain embodiments, the second database comprises scFv antibody $V_H$, $V_L$ or $V_H$ and $V_L$ amino acid sequences selected from a QC assay. In another embodiment the second database consists of scFv antibody $V_H$, $V_L$ or $V_H$ and $V_L$ amino acid sequences selected from a QC assay.

In one embodiment, the desirable functional property is improved stability. In another embodiment, the desirable functional property is improved solubility. In yet another embodiment, the desirable functional property is non-aggregation. In still another embodiment, the desirable functional property is an improvement in expression (e.g., in a prokaryotic cell). In certain embodiments, the desirable functional property is not an improvement in antigen binding affinity.

In yet another aspect, the invention provides a method of engineering an immunobinder, the method comprising:

a) selecting one or more amino acid positions within the immunobinder for mutation; and b) mutating the one more amino acid positions selected for mutation, wherein the one or more amino acid positions selected for mutation are selected from the group consisting of:

(i) amino acid positions 1, 6, 7, 89 and 103 of VH3 using AHo numbering (amino acid positions 1, 6, 7, 78 and 89 using Kabat numbering);

(ii) amino acid positions 1, 6, 12, 13, 14, 19, 21, 90, 92, 95 and 98 of VH1a using AHo numbering (amino acid positions 1, 6, 11, 12, 13, 18, 20, 79, 81, 82b and 84 using Kabat numbering);

(iii) amino acid positions 1, 10, 12, 13, 14, 20, 21, 45, 47, 50, 55, 77, 78, 82, 86, 87 and 107 of VH1b using AHo numbering (amino acid positions 1, 9, 11, 12, 13, 19, 20, 38, 40, 43, 48, 66, 67, 71, 75, 76 and 93 using Kabat numbering);

(iv) amino acid positions 1, 3, 4, 24, 47, 50, 57, 91 and 103 of Vκ1 using AHo numbering (amino acid positions 1, 3, 4, 24, 39, 42, 49, 73 and 85 using Kabat numbering);

(v) amino acid positions 2, 3, 10, 12, 18, 20, 56, 74, 94, 101 and 103 of Vκ3 using AHo numbering (amino acid positions 2, 3, 10, 12, 18, 20, 48, 58, 76, 83 and 85 using Kabat numbering); and (vi) amino acid positions 1, 2, 4, 7, 11, 14, 46, 53, 82, 92 and 103 of Vλ1 using AHo numbering (amino acid positions 1, 2, 4, 7, 11, 14, 38, 45, 66, 74 and 85 using Kabat numbering).

In certain preferred embodiments, the one or more amino acid positions selected for mutation are mutated to an amino acid residue found at a corresponding amino acid position in an antibody sequence selected as having at least one desirable functional property (e.g., in a yeast QC-System). In yet other embodiments, the one or more amino acid positions selected for mutation are mutated to an amino acid residue (e.g., an "enriched amino acid residue") identified according to the enrichment/exclusion analysis methodology of the invention.

Preferably, the immunobinder is a scFv, but other immunobinders, such as full-length immunoglobulins and other antibody fragments (e.g., Fabs or Dabs), also can be engineered according to the method. The invention also encompasses immunobinders prepared according to the engineering method, as well as compositions comprising the immunobinders and a pharmaceutically acceptable carrier.

BRIEF DESCRIPTION OF FIGURES

FIG. 4A depicts an exemplary soluble and stable scFv which, when fused to a functional transcription factor, is capable of triggering the transcription of a selectable marker. In contrast, FIG. 4B depicts the scenario whereby an unstable scFv hinders transcription of the selectable marker to be activated, even when fused to the transcription factor.

DETAILED DESCRIPTION OF THE INVENTION

Figure 1:
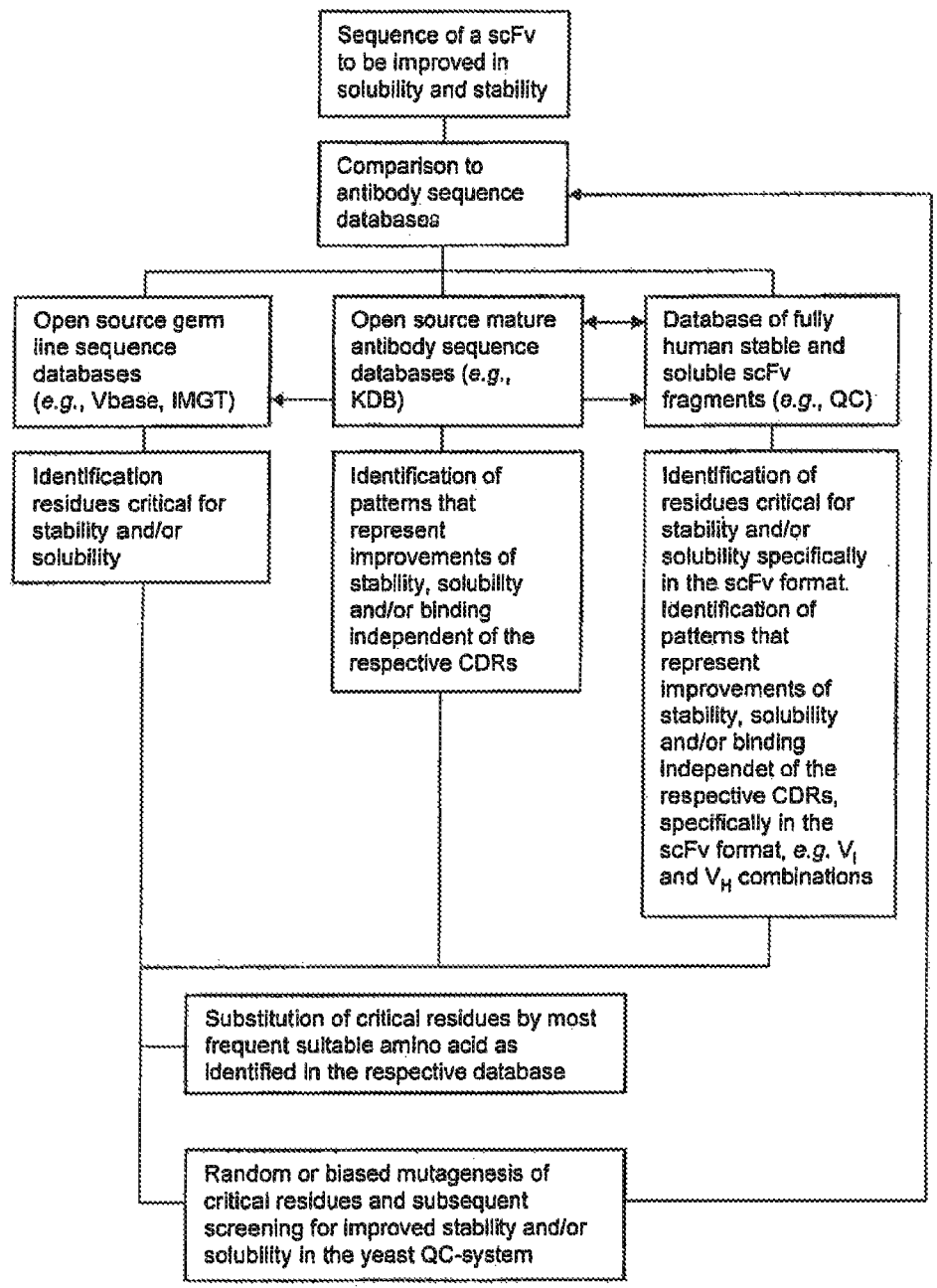
FIG. 1 is a flowchart diagram summarizing general sequence-based analyses of scFvs according to the methods of the invention.

The invention pertains to methods for sequence-based engineering and optimization of immunobinder properties, and in particular scFvs properties, including but not limited to, stability, solubility and affinity. More specifically, the present invention discloses methods for optimizing scFv antibodies using antibody sequence analysis to identify amino acid positions within a scFv to be mutated to thereby improve one or more physical properties of the scFv. The invention also pertains to engineered immunobinders, e.g., scFvs, produced according to the methods of the invention.

The invention is based, at least in part, on the analysis of the frequency of amino acids at each heavy and light chain framework position in multiple databases of antibody sequences. In particular, the frequency analysis of germline and/or mature antibody databases has been compared to the frequency analysis of a database of scFv sequences that have been selected as having desired functional properties. By assigning a degree of variability to each framework position (e.g., using the Simpson's Index) and by comparing the degree of variability at each framework position within the different types of antibody sequence databases, it has now been possible to identify framework positions of importance to the functional properties (e.g., stability, solubility) of a scFv. This now allows for defining a "functional consensus" to the framework amino acid positions, in which framework positions that are either more or less tolerant of variability than the corresponding positions in germline and/or mature antibody immunoglobulin sequences have been identified. Thus, the invention provides, and demonstrates the benefit of, a "functional consensus" approach based on the use of a database of functionally-selected scFv sequences. Still further, the invention provides methods of engineering immunobinders (e.g., scFvs) by mutating particular framework amino acid positions identified using the "functional consensus" approach described herein.

So that the invention may be more readily understood, certain terms are first defined. Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

The term "antibody" as used herein is a synonym for "immunoglobulin". Antibodies according to the present invention may be whole immunoglobulins or fragments thereof, comprising at least one variable domain of an immunoglobulin, such as single variable domains, Fv (Skerra A. and Pluckthun, A. (1988) *Science* 240:1038-41), scFv (Bird, R. E. et al. (1988) *Science* 242:423-26; Huston, J. S. et al. (1988) *Proc. Natl. Acad. Sci. USA* 85:5879-83), Fab, (Fab')2 or other fragments well known to a person skilled in the art.

The term "antibody framework" as used herein refers to the part of the variable domain, either VL or VH, which serves as a scaffold for the antigen binding loops of this variable domain (Kabat, E. A. et al., (1991) Sequences of proteins of immunological interest. NIH Publication 91-3242).

The term "antibody CDR" as used herein refers to the complementarity determining regions of the antibody which consist of the antigen binding loops as defined by Kabat E. A. et al., (1991) Sequences of proteins of immunological interest. NIH Publication 91-3242). Each of the two variable domains of an antibody Fv fragment contain, for example, three CDRs.

The term "single chain antibody" or "scFv" is intended to refer to a molecule comprising an antibody heavy chain variable region ($V_H$) and an antibody light chain variable region ($V_L$) connected by a linker. Such scFv molecules can have the general structures: $NH_2$-$V_L$-linker-$V_H$-COOH or $NH_2$-$V_H$-linker-$V_L$-COOH.

As used herein, "identity" refers to the sequence matching between two polypeptides, molecules or between two nucleic acids. When a position in both of the two compared sequences is occupied by the same base or amino acid monomer subunit (for instance, if a position in each of the two DNA molecules is occupied by adenine, or a position in each of two polypeptides is occupied by a lysine), then the respective molecules are identical at that position. The "percentage identity" between two sequences is a function of the number of matching positions shared by the two sequences divided by the number of positions compared× 100. For instance, if 6 of 10 of the positions in two sequences are matched, then the two sequences have 60% identity. By way of example, the DNA sequences CTGACT and CAGGTT share 50% identity (3 of the 6 total positions are matched). Generally, a comparison is made when two sequences are aligned to give maximum identity. Such alignment can be provided using, for instance, the method of Needleman et al. (1970) *J. Mol. Biol.* 48: 443-453, implemented conveniently by computer programs such as the Align program (DNAstar, Inc.).

"Similar" sequences are those which, when aligned, share identical and similar amino acid residues, where similar residues are conservative substitutions for corresponding amino acid residues in an aligned reference sequence. In this regard, a "conservative substitution" of a residue in a reference sequence is a substitution by a residue that is physically or functionally similar to the corresponding reference residue, e.g., that has a similar size, shape, electric charge, chemical properties, including the ability to form covalent or hydrogen bonds, or the like. Thus, a "conservative substitution modified" sequence is one that differs from a reference sequence or a wild-type sequence in that one or more conservative substitutions are present. The "percentage similarity" between two sequences is a function of the number of positions that contain matching residues or conservative substitutions shared by the two sequences divided by the number of positions compared×100. For instance, if 6 of 10 of the positions in two sequences are matched and 2 of 10 positions contain conservative substitutions, then the two sequences have 80% positive similarity.

"Amino acid consensus sequence" as used herein refers to an amino acid sequence that can be generated using a matrix of at least two, and preferably more, aligned amino acid sequences, and allowing for gaps in the alignment, such that it is possible to determine the most frequent amino acid residue at each position. The consensus sequence is that sequence which comprises the amino acids which are most frequently represented at each position. In the event that two or more amino acids are equally represented at a single position, the consensus sequence includes both or all of those amino acids.

The amino acid sequence of a protein can be analyzed at various levels. For example, conservation or variability can be exhibited at the single residue level, multiple residue level, multiple residue with gaps etc. Residues can exhibit conservation of the identical residue or can be conserved at the class level. Examples of amino acid classes include polar but uncharged R groups (Serine, Threonine, Asparagine and Glutamine); positively charged R groups (Lysine, Arginine, and Histidine); negatively charged R groups (Glutamic acid and Aspartic acid); hydrophobic R groups (Alanine, Isoleucine, Leucine, Methionine, Phenylalanine, Tryptophan, Valine and Tyrosine); and special amino acids (Cysteine, Glycine and Proline). Other classes are known to one of skill in the art and may be defined using structural determinations or other data to assess substitutability. In that sense, a substitutable amino acid can refer to any amino acid which can be substituted and maintain functional conservation at that position.

As used herein, when one amino acid sequence (e.g., a first $V_H$ or $V_L$ sequence) is aligned with one or more additional amino acid sequences (e.g., one or more VH or VL sequences in a database), an amino acid position in one sequence (e.g., the first $V_H$ or $V_L$ sequence) can be compared to a "corresponding position" in the one or more additional amino acid sequences. As used herein, the "corresponding position" represents the equivalent position in the sequence(s) being compared when the sequences are optimally aligned, i.e., when the sequences are aligned to achieve the highest percent identity or percent similarity.

As used herein, the term "antibody database" refers to a collection of two or more antibody amino acid sequences (a "multiplicity" of sequences), and typically refers to a collection of tens, hundreds or even thousands of antibody amino acid sequences. An antibody database can store amino acid sequences of, for example, a collection of antibody $V_H$ regions, antibody $V_L$ regions or both, or can store a collection of scFv sequences comprised of $V_H$ and $V_L$ regions. Preferably, the database is stored in a searchable, fixed medium, such as on a computer within a searchable computer program. In one embodiment, the antibody database is a database comprising or consisting of germline antibody sequences. In another embodiment, the antibody database is a database comprising or consisting of mature (i.e., expressed) antibody sequences (e.g., a Kabat database of mature antibody sequences, e.g., a KBD database). In yet another embodiment, the antibody database comprises or consists of functionally selected sequences (e.g., sequences selected from a QC assay).

The term "immunobinder" refers to a molecule that contains all or a part of the antigen binding site of an antibody, e.g., all or part of the heavy and/or light chain variable domain, such that the immunobinder specifically recognizes a target antigen. Non-limiting examples of immunobinders include full-length immunoglobulin molecules and scFvs, as well as antibody fragments, including but not limited to (i) a Fab fragment, a monovalent fragment consisting of the $V_L$, $V_H$, $C_L$ and $C_H1$ domains; (ii) a F(ab')$_2$ fragment, a bivalent fragment comprising two Fab fragments linked by a disulfide bridge at the hinge region; (iii) a Fab' fragment, which is essentially a Fab with part of the hinge region (see, FUNDAMENTAL IMMUNOLOGY (Paul ed., 3.sup.rd ed. 1993); (iv) a Fd fragment consisting of the $V_H$ and $C_H1$ domains; (v) a Fv fragment consisting of the $V_L$ and $V_H$ domains of a single arm of an antibody, (vi) a dAb fragment (Ward et al., (1989) *Nature* 341:544-546), which consists of a $V_H$ domain; and (vii) a nanobody, a heavy chain variable region containing a single variable domain and two constant domains.

As used herein, the term "functional property" is a property of a polypeptide (e.g., an immunobinder) for which an improvement (e.g., relative to a conventional polypeptide) is desirable and/or advantageous to one of skill in the art, e.g., in order to improve the manufacturing properties or therapeutic efficacy of the polypeptide. In one embodiment, the functional property is improved stability (e.g., thermal stability). In another embodiment, the functional property is improved solubility (e.g., under cellular conditions). In yet another embodiment, the functional property is non-aggregation. In still another embodiment, the functional property is an improvement in expression (e.g., in a prokaryotic cell). In yet another embodiment the functional property is an improvement in refolding yield following an inclusion body purification process. In certain embodiments, the functional property is not an improvement in antigen binding affinity.

Sequence Based Analysis of scFvs

The invention provides methods for analyzing a scFv sequence that allow for the identification of amino acid positions within the scFv sequence to be selected for mutation. The amino acid positions selected for mutation are ones that are predicted to influence functional properties of the scFv, such as solubility, stability and/or antigen binding, wherein mutation at such positions is predicted to improve the performance of the scFv. Thus, the invention allows for more focused engineering of scFvs to optimize performance than simply randomly mutating amino acid positions within the scFv sequence.

Certain aspects of the sequence-based analysis of scFv sequences are diagrammed schematically in the flowchart of FIG. 1. As shown in this figure, the sequence of a scFv to be optimized is compared to the sequences in one or more antibody databases, including an antibody database composed of scFv sequences selected as being stable and soluble. This can allow for identification of residues critical for stability and/or solubility specifically in the scFv format, a well as identification of patterns that represent improvements in stability, solubility and/or binding independent of the respective CDRs, specifically in the scFv format (e.g., $V_L$ and $V_H$ combinations). Once critical residues have been identified, they can be substituted by, for example, the most frequent suitable amino acid as identified in the respective database and/or by random or biased mutagenesis.

Thus, in one aspect, the invention pertains to a method of identifying an amino acid position for mutation in a single chain antibody (scFv), the scFv having $V_H$ and $V_L$ amino acid sequences, the method comprising:

a) entering the scFv $V_H$, $V_L$ or $V_H$ and $V_L$ amino acid sequences into a database that comprises a multiplicity of antibody $V_H$, $V_L$ or $V_H$ and $V_L$ amino acid sequences such that the scFv $V_H$, $V_L$ or $V_H$ and $V_L$ amino acid sequences are aligned with the antibody $V_H$, $V_L$ or $V_H$ and $V_L$ amino acid sequences of the database;

b) comparing an amino acid position within the scFv $V_H$ or $V_L$ amino acid sequence with a corresponding position within the antibody $V_H$ or $V_L$ amino acid sequences of the database;

c) determining whether the amino acid position within the scFv $V_H$ or $V_L$ amino acid sequence is occupied by an amino acid residue that is conserved at the corresponding position within the antibody $V_H$ or $V_L$ amino acid sequences of the database; and d) identifying the amino acid position within the scFv $V_H$ or $V_L$ amino acid sequence as an amino acid position for mutation when the amino acid position is occupied by an amino acid residue that is not conserved at the corresponding position within the antibody $V_H$ or $V_L$ amino acid sequences of the database.

Thus, in the method of the invention, the sequence of a scFv of interest (i.e., the sequence of the $V_H$, $V_L$ or both) is compared to the sequences of an antibody database and it is determined whether an amino acid position in the scFv of interest is occupied by an amino acid residue that is "conserved" in the corresponding position of the sequences in the database. If the amino acid position of the scFv sequence is occupied by an amino acid residue that is not "conserved" at the corresponding position within the sequences of the database, then that amino acid position of the scFv is chosen for mutation. Preferably, the amino acid position that is analyzed is a framework amino acid position within the scFv of interest. Even more preferably, every framework amino acid position within the scFv of interest can be analyzed. In an alternative embodiment, one or more amino acid positions within one or more CDRs of the scFv of interest can be analyzed. In yet another embodiment, each amino acid position with the scFv of interest can be analyzed.

To determine whether an amino acid residue is "conserved" at a particular amino acid position within the sequences of the antibody database (e.g., a framework position), the degree of conservation at the particular position can be calculated. There are a variety of different ways known in the art that amino acid diversity at a given position can be quantified, all which can be applied to the methods of the present invention. Preferably, the degree of conservation is calculated using Simpson's diversity index, which is a measure of diversity. It takes into account the number of amino acids present at each position, as well as the relative abundance of each amino acid. The Simpson Index (S.I.) represents the probability that two randomly selected antibody sequences contain the same amino acid at certain positions. The Simpson Index takes into account two main factors when measuring conservation, richness and evenness. As used herein, "richness" is a measure of the number of different kinds of amino acids present in a particular position (i.e., the number of different amino acid residues represented in the database at that position is a measure of richness). As used herein, "evenness" is a measure of the abundance of each of the amino acids present at the particular position (i.e., the frequency with which amino acid residues occur that position within the sequences of the database is a measure of evenness).

While residue richness can be used as a measure on its own to examine degree of conservation at a particular position, it does not take into account the relative frequency of each amino acid residue present at a certain position. It gives as much weight to those amino acid residues that occur very infrequently at a particular position within the sequences of a database as it does to those residues that occur very frequently at the same position. Evenness is a measure of the relative abundance of the different amino acids making up the richness of a position. The Simpson Index takes both into account, richness and evenness, and thus is a preferred way to quantitate degree of conservation according to the present invention. In particular, low frequent residues at very conserved positions are considered as potentially problematic and thus can be chosen for mutation.

The formula for the Simpson index is $D=\Sigma n_i(n_i-1)/N(N-1)$, wherein N is the total number of sequences in the survey (e.g., in the database) and $n_i$ is the frequency of each amino acid residue at the position being analyzed. The frequency of an amino acid event (i) in the database is the number $(n_i)$ of times the amino acid occurred in the database. The counts $n_i$ themselves are given in relative frequencies, which means they are normalized by the total number of events. When maximum diversity occurs, the S.I. value is zero and when minimum diversity occurs, the S.I. value is 1. Thus, the S.I. range is 0-1, with an inverse relationship between diversity and the index value.

Figure 2:
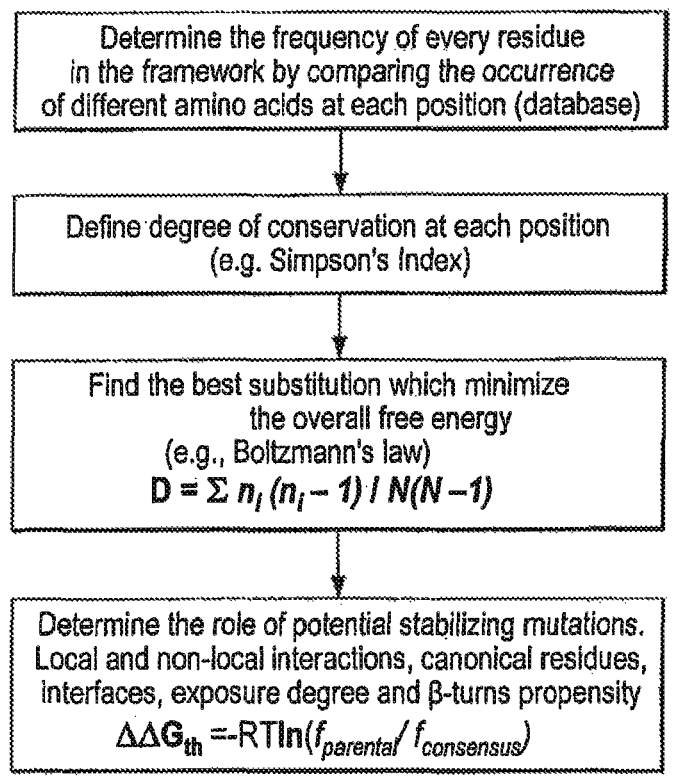
FIG. 2 is a flowchart diagram of an exemplary multi-step method for sequence-based analysis of scFvs.

A flow chart summarizing the multiple steps for analysis of framework amino acid positions within the sequences of the database is described in further detail in FIG. 2.

Accordingly, in a preferred embodiment of the above-described method, the corresponding position within the antibody $V_H$ or $V_L$ amino acid sequence of the database is assigned a degree of conservation using Simpson's Index. The S.I. value of that corresponding position can be used as an indicator of the conservation of that position.

In other embodiments, trusted alignments of closely related antibody sequences are used in the present invention to generate matrices of relative abundance of amino acids and degree of conservation of determined positions. These matrices are designed for use in antibody-antibody database comparisons. The observed frequency of each residue is calculated and compared to the expected frequencies (which are essentially the frequencies of each residue in the dataset for each position).

Analysis of a given scFv antibody with the described method provides information about biologically permissible mutations and unusual residues at certain positions in the given scFv antibody and allows the prediction of potential weakness within its framework. The routine can be used to engineer amino acid substitutions that "best" fit a set of amino acid-frequency data, using the S.I. value and the relative frequency as a criterion.

The sequence-based analysis described above can be applied to the $V_H$ region of the scFv, to the $V_L$ region of the scFv, or to both. Thus, in one embodiment, scFv $V_H$ amino acid sequence is entered into the database and aligned with antibody $V_H$ amino acid sequences of the database. In another embodiment, the scFv $V_L$ amino acid sequence is entered into the database and aligned with antibody $V_L$ amino acid sequences of the database. In yet another embodiment, the scFv $V_H$ and $V_L$ amino acid sequences are entered into the database and aligned with antibody $V_H$ and $V_L$ amino acid sequences of the database. Algorithms for aligning one sequence with a collection of other sequences in a database are well-established in the art. The sequences are aligned such that the highest percent identity or similarity between the sequences is achieved.

The methods of the invention can be used to analyze one amino acid position of interest within a scFv sequence or, more preferably, can be used to analyze multiple amino acid positions of interest. Thus, in step b) of the above-described method, multiple amino acid positions within the scFv $V_H$ or $V_L$ amino acid sequence can be compared with corresponding positions within the antibody $V_H$ or $V_L$ amino acid sequences of the database. Preferred positions to be analyzed are framework positions within the $V_H$ and/or $V_L$ sequences of the scFv (e.g., each VH and VL framework position can be analyzed). Additionally or alternatively, one or more positions within one or more CDRs of the scFv can be analyzed (although it may not be preferred to mutate amino acid positions with the CDRs, since mutations within the CDRs are more likely to affect antigen binding activity than mutations within the framework regions). Still further, the methods of the invention allow for the analysis of each amino acid position within the scFv $V_H$, $V_L$ or $V_H$ and $V_L$ amino acid sequences.

In the methods of the invention, the sequence of a scFv of interest can be compared to the sequences within one or more of a variety of different types of antibody sequence databases. For example, in one embodiment, the antibody $V_H$, $V_L$ or $V_H$ and $V_L$ amino acid sequences of the database are germline antibody $V_H$, $V_L$ or $V_H$ and $V_L$ amino acid sequences. In another embodiment, the antibody $V_H$, $V_L$ or $V_H$ and $V_L$ amino acid sequences of the database are rearranged, affinity matured antibody $V_H$, $V_L$ or $V_H$ and $V_L$ amino acid sequences. In yet another, preferred embodiment, the antibody $V_H$, $V_L$ or $V_H$ and $V_L$ amino acid sequences of the database are scFv antibody $V_H$, $V_L$ or $V_H$ and $V_L$ amino acid sequences selected as having at least one desirable functional property, such as scFv stability or scFv solubility (discussed further below).

Antibody sequence information can be obtained, compiled, and/or generated from sequence alignments of germ line sequences or from any other antibody sequence that occurs in nature. The sources of sequences may include but are not limited to one or more of the following databases

- The Kabat database (.immuno. bme. nwu. edu; Johnson & Wu (2001) *Nucleic Acids Res.* 29: 205-206; Johnson & Wu (2000) *Nucleic Acids Res.* 28: 214-218). The raw data from 2000 are available by FTP in the US and mirrored in the UK.
- Kabatman contains a database that allows the user to search the Kabat sequence for sequence unusual features and enables the user to find canonical assignments for the CDRs in a specific antibody sequence.
- AAAAA Website (www.bioc.unizh.ch/antibody/), an antibody page prepared by Annemarie Honegger that provides sequence information and structural data on antibodies.
- ABG: Directory of 3D structures of antibodies—The directory, created by the Antibody Group (ABG), allows the user to access the antibody structures compiled at Protein Data Bank (PDB). In the directory, each PDB entry has a hyperlink to the original source to make full information recovering easy
- ABG: Germline gene directories of the mouse VH and VK germline segments, part of the webpage of the Antibody Group at the Instituto de Biotecnologia, UNAM (National University of Mexico)
- IMGT®, the international ImMunoGeneTics Information System®—created in 1989 by Marie-Paule Lefranc (Université Montpellier II, CNRS), IMGT is an integrated knowledge resource specialized in immunoglobulins, T cell receptors, and related proteins of the immune system for human and other vertebrate species. IMGT consists of sequence databases (IMGT/LIGM-DB, a comprehensive database of IG and TR from human and other vertebrates, with translation for fully annotated sequences, IMGT/MHC-DB, IMGT/PRIMER-DB), a genome database (IMGT/GENE-DB), a structure database (IMGT/3Dstructure-DB), a web resource (IMGT Repertoire) (IMGT, the internationalImMunoGeneTics informationsystem@; imgt. cines. fr; Lefranc et al. (1999) *Nucleic Acids Res.* 27: 209-212; Ruiz et al. (2000) *Nucleic Acids Res.* 28: 219-221; Lefranc et al. (2001) *Nucleic Acids Res.* 29: 207-209; Lefranc et al. (2003) *Nucleic Acids Res.* 31: 307-310).
- V BASE—a comprehensive directory of all human germline variable region sequences compiled from over a thousand published sequences, including those in the current releases of the Genbank and EMBL data libraries.

In a preferred embodiment, the antibody sequence information is obtained from a scFv library having defined frameworks that have been selected for enhanced stability and solubility in a reducing environment. More specifically, a yeast Quality Control (QC)—System has been described (see e.g., PCT Publication WO 2001/48017; U.S. Application Nos. 2001/0024831 and US 2003/0096306; U.S. Pat. Nos. 7,258,985 and 7,258,986) that allows for the selection of scFv frameworks with enhanced stability and solubility in a reducing environment. In this system, a scFv library is transformed into host cells able to express a specific known antigen and only surviving in the presence of antigen-scFv interaction. The transformed host cells are cultivated under conditions suitable for expression of the antigen and the scFv and allowing for cell survival only in the presence of antigen-scFv interaction. Thus, scFvs expressed in the surviving cells and having defined frameworks that are stable and soluble in a reducing environment can be isolated. Accordingly, the QC-System can be used to screen a large scFv library to thereby isolate those preferred scFvs having frameworks that are stable and soluble in a reducing environment and the sequences of those selected scFvs can be compiled into a scFv sequence database. Such a scFv database then can be used for comparison purposes with other scFv sequences of interest using the methods of the instant invention. Preferred scFv framework sequences that have previously selected and defined using the QC-System are described in further detail in PCT Publication WO 2003/097697 and U.S. Application No. 20060035320.

Figure 3:
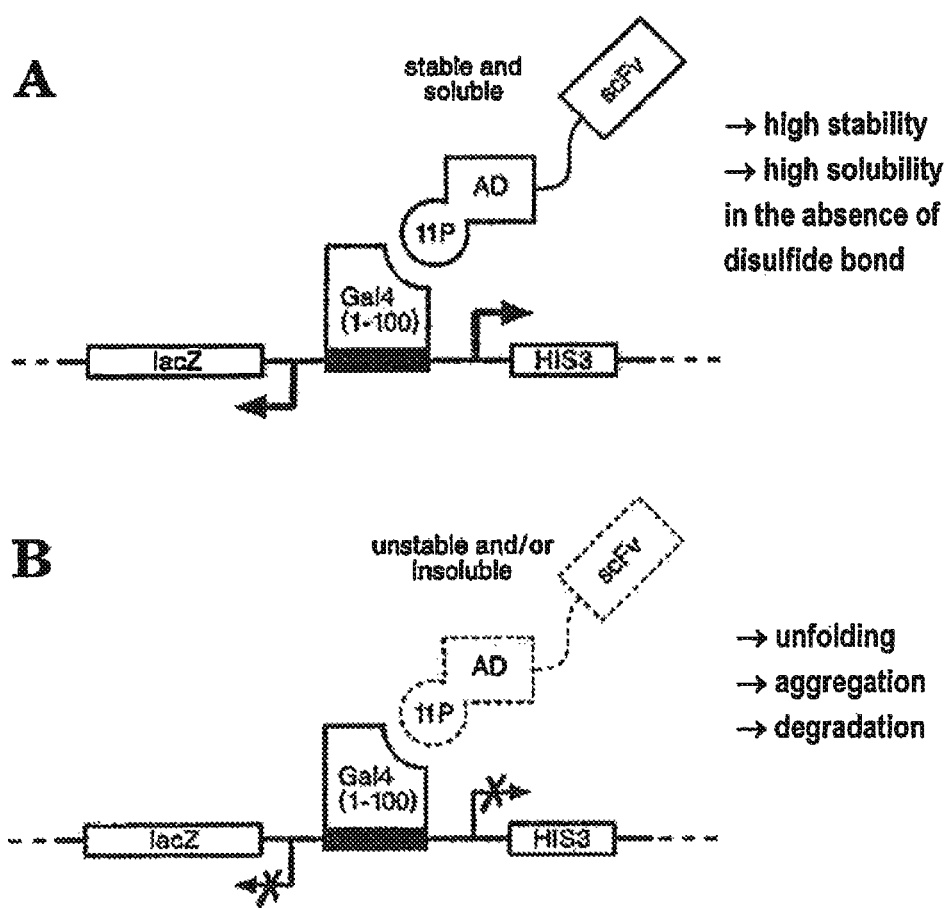
FIG. 3 is a schematic diagram of an exemplary Quality Control (QC) system for selection of stable and soluble scFvs in yeast. With this system, host cells capable of expressing stable and soluble scFvs in a reducing environment are selected due to the presence of an inducible reporter construct which expression is dependent on the presence of a stable and soluble scFv-AD-Gal 11p fusion protein. Interaction of the fusion protein with Gal4 (1-100) forms a functional transcription factor which activates expression of a selectable marker (see FIG. 3A). Unstable and/or insoluble scFvs are incapable of forming a functional transcription factor and inducing expression of the selectable marker and are therefore excluded from selection (FIG. 3B).

Variants of the original QC-System are known in the art. In one exemplary embodiment, which is illustrated schematically in FIG. 3, a scFv library is fused to the activation domain (AD) of the Gal4 yeast transcription factor, which is in turn fused to a portion of the so-called Gal11p protein (11p). The scFv-AD-Gal11p fusion construct is then transformed into host cells that express the first 100 amino acids of Gal 4 and thus contain the Gal4 DNA-binding domain (DBD; Gal4(1-100)). Gal11p is a point mutation that is known to directly bind to Gal4(1-100) (see Barberis et al., Cell, 81: 359 (1995)). The transformed host cells are cultivated under conditions which are suitable for expression of the scFv fusion protein and that allow for cell survival only in the case that the scFv fusion protein is stable and soluble enough to interact with Gal4(1-100) and thereby form a functional transcription factor containing an AD linked to a DBD (FIG. 3A). Thus, scFvs expressed in the surviving cells and having defined frameworks that are stable and soluble in a reducing environment can be isolated. A further description of this exemplary QC system is described in Auf der Maur et al., Methods, 34: 215-224 (2004).

Figure 4:
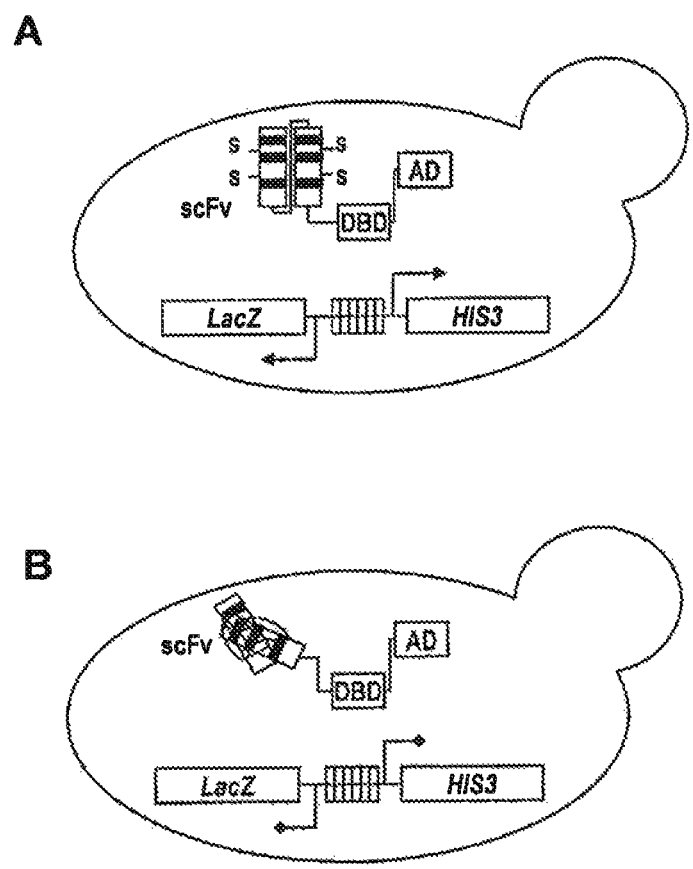
FIG. 4 is a schematic diagram of another exemplary Quality Control (QC) system. The overall concept for selecting soluble and scFv is the same as described for FIG. 3, however in this version, the scFv is directly fused to a functional transcription factor comprising an activation domain (AD) and a DNA-binding domain (DBD).

In another exemplary embodiment, a QC-system employed in the methods of the invention is depicted in FIG. 4. In this version of the QC-system, the scFv or the scFv library is directly fused to a functional transcription factor and expressed in a yeast strain containing a selectable marker. The selectable marker will only by activated in the presence of a functional scFv-transcription factor fusion, which means that the construct as a whole needs to be stable and soluble (FIG. 4A). In the event that the scFv is unstable, it will form aggregates and eventually be degraded, thereby also causing degradation of the transcription factor fused to it so that it is no longer able to activate the expression of the selectable marker (see FIG. 4B).

In the methods of the invention, the sequence of a scFv of interest can be compared with all sequences within an antibody database or, alternatively, only a selected portion of the sequences in the database can be used for comparison purposes. That is, the database can be limited, or constrained, to only those sequences having a high percentage similarity or identity to the scFv of interest. Thus, in one embodiment of the method of the invention, the database is a constrained database in which only those antibody $V_H$, $V_L$ or $V_H$ and $V_L$ amino acid sequences having high similarity to the scFv antibody $V_H$, $V_L$ or $V_H$ and $V_L$ amino acid sequences are included in the database.

Once the scFv sequence of interest is entered into the database and compared to the antibody sequences within the database, sequence information is analyzed to provide information about the frequency and variability of amino acids of a given position and to predict potentially problematic amino acid positions, in particular potentially problematic amino acid positions within the framework of the scFv. Such information can also be used to design mutations that improve the properties of the scFv. For example antibody solubility can be improved by replacing solvent exposed hydrophobic residues by hydrophilic residues that otherwise occur frequently at this position.

In the method of the invention, there are a number of possible types of amino acid residues that can be "conserved" at a particular position within the antibody sequences of the database. For example, one particular amino acid residue may be found at that position at a very high frequency, indicating that this particular amino acid residue is preferred at that particular position. Accordingly, in one embodiment of the method, in step c), the amino acid residue that is conserved at the corresponding position within the antibody $V_H$ or $V_L$ amino acid sequences of the database is the amino acid residue that is most frequently at that position within the antibody $V_H$ or $V_L$ amino acid sequences of the database. In other embodiments, the position may be "conserved" with a particular type or class of amino acid residue (i.e., the position is not preferentially occupied by only a single particular amino acid residue, but rather is preferentially occupied by several different amino acid residues each of which is of the same type or class of residue). For example, in step c), the corresponding position within the antibody $V_H$ or $V_L$ amino acid sequences of the database may be conserved with: (i) hydrophobic amino acid residues, (ii) hydrophilic amino acid residues, (iii) amino acid residues capable of forming a hydrogen bond or (iv) amino acid residues having a propensity to form a β-sheet.

In step d) of the method, an amino acid position within the scFv $V_H$ or $V_L$ amino acid sequence is identified as an amino acid position for mutation when the amino acid position is occupied by an amino acid residue that is not conserved at the corresponding position within the antibody $V_H$ or $V_L$ amino acid sequences of the database. There are a number of possible situations that would identify an amino acid position as being occupied by an amino acid residue that is "not conserved" and thus as being potentially problematic. For example, if the corresponding amino acid position within the database is conserved with a hydrophobic residue and the position in the scFv is occupied by a hydrophilic residue, this position could be potentially problematic in the scFv and the position can be selected for mutation. Likewise, if the corresponding amino acid position within the database is conserved with a hydrophilic residue and the position in the scFv is occupied by a hydrophobic residue, this position could be potentially problematic in the scFv and the position can be selected for mutation. In still other instances, if the corresponding amino acid position within the database is conserved with amino acid residues that are capable of forming a hydrogen bond or that have a propensity to form a β sheet, and the position in the scFv is occupied by a residue that is not capable of forming a hydrogen bond or does not have a propensity to form a β sheet, respectively, this position could be potentially problematic in the scFv and the position can be selected for mutation.

In a preferred embodiment, the methods described in the present invention can be used alone or in combination to create combinatorial lists of amino acid substitutions to improve stability and or solubility of antibody single chain fragments.

Covariance Analysis

The invention also pertains to methods for analyzing covariance within the sequence of a scFv as compared to antibody sequences within a database. Residues which covary can be, for example, (i) a residue in a framework region (FR) and a residue in a CDR; (ii) a residue in one CDR and a residue in another CDR; (iii) a residue in one FR and a residue in another FR; or (iv) a residue in the $V_H$ and a residue in the $V_L$. Residues which interact with each other in the tertiary structure of the antibody may covary such that preferred amino acid residues may be conserved at both positions of the covariant pair and if one residue is altered the other residue must be altered as well to maintain the antibody structure. Methods for conducting a covariance analysis on a set of amino acid sequences are known in the art. For example, Choulier, L. et al. (2000) *Protein* 41:475-484 describes applying a covariance analysis to human and mouse germline $V_\kappa$ and $V_H$ sequence alignments.

A covariance analysis can be combined with the above-described method for analyzing conserved amino acid positions (steps a)-d) in the method above), such that the method further comprises the steps:

e) carrying out a covariance analysis on the antibody $V_H$ or $V_L$ amino acid sequence of the database to identify a covariant pair of amino acid positions;

f) comparing the covariant pair of amino acid positions with corresponding positions within the scFv $V_H$ or $V_L$ amino acid sequence;

g) determining whether the corresponding positions within the scFv $V_H$ or $V_L$ amino acid sequence are occupied by amino acid residues that are conserved at the covariant pair of amino acid positions within the antibody $V_H$ or $V_L$ amino acid sequences of the database; and h) identifying one or both of the corresponding positions within the scFv $V_H$ or $V_L$ amino acid sequence as an amino acid position for mutation when one or both of the corresponding positions within the scFv is occupied by an amino acid residue that is not conserved at the covariant pair of amino acid positions within the antibody $V_H$ or $V_L$ amino acid sequences of the database.

Additionally or alternatively, a covariance analysis can be conducted on its own, such that the invention provides a method comprising the steps:

a) carrying out a covariance analysis on antibody $V_H$ or $V_L$ amino acid sequences of a database to identify a covariant pair of amino acid positions;

b) comparing the covariant pair of amino acid positions with corresponding positions within a scFv $V_H$ or $V_L$ amino acid sequence;

c) determining whether the corresponding positions within the scFv $V_H$ or $V_L$ amino acid sequence are occupied by amino acid residues that are conserved at the covariant pair of amino acid positions within the antibody $V_H$ or $V_L$ amino acid sequences of the database; and d) identifying one or both of the corresponding positions within the scFv $V_H$ or $V_L$ amino acid sequence as an amino acid position for mutation when one or both of the corresponding positions within the scFv is occupied by an amino acid residue that is not conserved at the covariant pair of amino acid positions within the antibody $V_H$ or $V_L$ amino acid sequences of the database.

The covariance analysis methods of the invention can be used to analyze one covariant pair, or more than one covariant pair. Thus, in one embodiment of the method, multiple covariant pairs of amino acid positions are identified within the antibody $V_H$ or $V_L$ amino acid sequence of the database and compared to the corresponding positions within the scFv $V_H$ or $V_L$ amino acid sequence.

The method can further comprise mutating one or both of the corresponding positions within the scFv that are occupied by an amino acid residue that is not conserved at the covariant pair of amino acid positions within the antibody $V_H$ or $V_L$ amino acid sequences of the database. In one embodiment, one of the corresponding positions within the scFv that is occupied by an amino acid residue that is not conserved at the covariant pair of amino acid positions is substituted with an amino acid residue that is most frequently at the covariant pair amino acid position. In another embodiment, both of the corresponding positions within the scFv that are occupied by amino acid residues that are not conserved at the covariant pair of amino acid positions are substituted with amino acid residues that are most frequently at the covariant pair amino acid positions.

Molecular Modeling

The sequence-based methods of the invention for analyzing scFvs for potentially problematic residues can be combined with other methods known in the art for analyzing antibody structure/function relationships. For example, in a preferred embodiment, the sequence-based analytical methods of the invention are combined with molecular modeling to identify additional potentially problematic residues. Methods and software for computer modeling of antibody structures, including scFv structures, are established in the art and can be combined with the sequence-based methods of the invention. Thus, in another embodiment, the sequence-based methods described above as set forth in steps a)-d) further comprise the steps of:

e) subjecting the scFv $V_H$, $V_L$ or $V_H$ and $V_L$ amino acid sequences to molecular modeling; and f) identifying at least one additional amino acid position within the scFv $V_H$, $V_L$ or $V_H$ and $V_L$ amino acid sequences for mutation.

The method can further comprise mutating the at least one additional amino acid position within scFv $V_H$, $V_L$ or $V_H$ and $V_L$ amino acid sequences identified for mutation by molecular modeling.

"Functional Consensus" Versus "Conventional Consensus" Analysis

Figure 5:
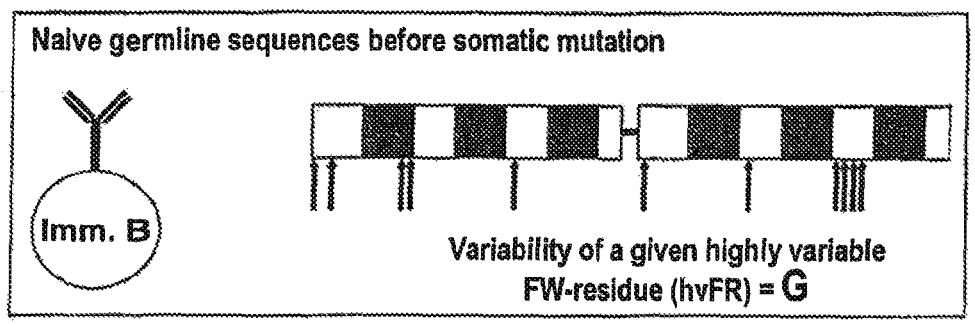
FIG. 5 is schematic diagram of the analysis of variability at particular framework (FW) residues within native germline sequences before somatic mutation (FIG. 5A) and at the corresponding FW residues within mature antibody sequences after somatic mutation selected in the QC system (FIG. 5B). Different variability values can be assigned to the respective FW positions (e.g., highly variable framework residues ("hvFR")) within the germline and QC sequences (i.e., "G" and "Q" values, respectively). If G>Q for a particular position, there is a restricted number of suitable stable FW residues at that position. If G<Q for a particular position, this may indicate that the residue has been naturally selected for optimal solubility and stability.
Figure 5:
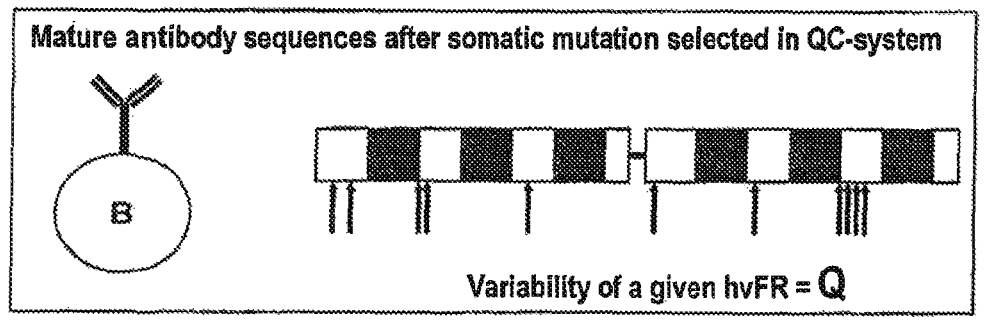

In a particularly preferred embodiment, the degree of variability at one or more framework positions is compared between a first database of antibody sequences (e.g., a germline database(s)(e.g., Vbase and/or IMGT) or a mature antibody database (e.g., KBD) and a second database of scFvs selected as having one or more desirable properties, e.g., a database of scFvs selected by QC screening in yeast, i.e., a QC database. As illustrated in FIG. 5, a variability value (e.g., Simpson's Index value) can be assigned to framework positions within the first (e.g., germline) database, referred to as "G" values in FIG. 5, and a variability value (e.g., Simpson's Index value) can be assigned to the corresponding framework positions within the second database (e.g., QC database), referred to as "Q" values in FIG. 5. When the G value is greater than the Q value at a particular position (i.e., more variability in the germline sequences at that position than in the selected scFv sequences), this indicates that there are a restricted number of stable scFv framework amino acid residues at that position, which stable scFv framework amino acid residues may be suitable for use with any CDRs. Alternatively, when the G value is less than the Q value at a particular position (i.e., more variability in the selected scFv sequences at that position than in the germline sequences), this indicates that this particular position is more tolerant of variability in the scFv and thus may represent a position at which amino acid substitutions may optimize stability and/or solubility of the scFv. Table 12 presents a summary table of the number of amino acid positions, and highly variable framework residues (hvFR), at which either G is greater than Q or G is less than Q. As indicated in Table 12, the variability in total number of amino acids (Aa #) and in highly variable framework residues (hvFRs) is significantly increased between germline and QC-FWs.

TABLE 12

Summary Table

|  | Aa # | G < Q (#of cases) | G > Q (#of cases) | X/Y | #hvFR (Simpson <0.4) | G < Q (#of cases) | G > Q (#of cases) | X/Y |
|---|---|---|---|---|---|---|---|---|
| $V_L$ | 108 | 61 | 11 | 5.5 | 16 | 13 | 3 | 4.3 |
| $V_H$ | 116 | 50 | 18 | 2.8 | 27 | 22 | 5 | 4.4 |

In view of the foregoing, in yet another aspect, the invention provides a method of identifying one or more framework amino acid positions for mutation in a single chain antibody (scFv), the scFv having $V_H$ and $V_L$ amino acid sequences, the method comprising:

a) providing a first database of $V_H$, $V_L$ or $V_H$ and $V_L$ amino acid sequences (e.g., germline and/or mature antibody sequences);

b) providing a second database of scFv antibody $V_H$, $V_L$ or $V_H$ and $V_L$ amino acid sequences selected as having at least one desirable functional property;

c) determining amino acid variability at each framework position of the first database and at each framework position of the second database;

d) identifying one or more framework positions at which degree of amino acid variability differs between the first database and the second database to thereby identify one or more framework amino acid positions for mutation in a single chain antibody (scFv).

Preferably, the amino acid variability at each framework position is determined by assigning a degree of conservation using Simpson's Index. In one embodiment, the one or more framework amino acid positions is identified for mutation based on the one or more framework amino acid positions having a lower Simpson's Index value in the second (scFv) database as compared to the first database. In another embodiment, the one or more framework amino acid positions is identified for mutation based on the one or more framework amino acid positions having a higher Simpson's Index value in the second database as compared to the first database.

Variability analyses, and identification of residues for mutation, for three human $V_H$ families and three human $V_L$ families are described in further detail in Examples 2 and 3 below.

Enrichment/Exclusion Analysis

In another aspect, the invention provides methods for selecting preferred amino acid residue substitutions (or, alternatively, excluding particular amino acid substitutions) at a framework position of interest within an immunobinder (e.g., to improve a functional property such as stability and/or solubility). The methods of the invention compare the frequency of an amino acid residue at a framework position of interest in a first database of antibody sequences (e.g., germline database(s) such Vbase and/or IMGT or, more preferably, a mature antibody database such as the Kabat database (KBD)) with the frequency of the amino acid residue at a corresponding amino acid position in a second database of scFvs selected as having one or more desirable properties, e.g., a database of scFvs selected by QC screening in yeast, i.e., a QC database.

As described in detail in Example 4 below, antibody sequences (e.g., VH or VL sequences) from the first database (e.g., a database of mature antibody sequences) may be grouped according to their Kabat family subtype (e.g., Vh1b, VH3, etc.). Within each sequence subtype (i.e., subfamily), the frequency of each amino acid residue (e.g., A, V, etc.) at each amino acid position is determined as a percentage of all the analyzed sequences of that subtype. The same is done for all the sequences of the second database (i.e., a database of scFvs selected as having one or more desirable properties, e.g., by QC screening). For each subtype, the resulting percentages (relative frequencies) for each amino acid residue type at a particular position are compared between the first and second databases. Where the relative frequency of a certain amino acid residue is increased in the second database (e.g., a QC database) relative to the first database (e.g., Kabat database), this indicates that the respective residue is favorably selected (i.e., an "enriched residue") and imparts favorable properties to the sequence. Conversely, where the relative frequency of the amino acid residue is decreased in the second database relative to the first database, this indicates that the respective residue is disfavored (i.e., an "excluded residue"). Accordingly, enriched residues are preferred residues for improving the functional properties (e.g., stability and/or solubility) of an immunobinder, while excluded residues are preferably avoided.

In view of the foregoing, in one embodiment, the invention provides a method of identifying a preferred amino acid residue for substitution in an immunobinder, the method comprising:

a) providing a first database of grouped $V_H$ or $V_L$ amino acid sequences (e.g., germline and/or mature antibody sequences grouped according to Kabat family subtype);

b) providing a second database of grouped scFv antibody $V_H$ or $V_L$ amino acid sequences selected as having at least one desirable functional property (e.g., according to QC assay);

c) determining amino acid frequency for an amino acid residue at a framework position of the first database and at a corresponding framework position of the second database;

d) identifying the amino acid residue as a preferred amino acid residue for substitution at a corresponding amino acid position of the immunobinder when the amino acid residue occurs at a higher frequency in the second database relative to the first database (i.e., an enriched residue).

The enrichment of an amino acid residue in the second (scFv) database (e.g., a QC database) can be quantified. For example, the ratio between the relative frequency of a residue within the second database (RF2) and the relative frequency of a residue within the first database (RF1) can be determined. This ratio (RF2:RF1) may be termed an "enrichment factor" (EF). Accordingly, in certain embodiments, the amino acid residue in step (d) is identified if the ratio of the relative frequency of the amino acid residue between the first and second databases (herein, the "enrichment factor") is at least 1 (e.g., 1, 2, 3, 4, 5, 6, 7, 8, 9 or 10). In a preferred embodiment, the enrichment factor is greater than about 1.0 (e.g. 1.0, 1.1, 1.2, 1.3, 1.4 or 1.5). In yet another preferred embodiment, the enrichment factor is about 4.0 to about 6.0 (e.g., 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9 or 6.0). In another embodiment, the enrichment factor is about 6.0 to about 8.0 (e.g., 6.0, 6.1, 6.2, 6.3, 6.4, 6.5, 6.6, 6.7, 6.8, 6.9, 7.0, 7.1, 7.3, 7.4, 7.5, 7.6, 7.7, 7.8, 7.9 or 8.0).

In another embodiment, the invention provides a method of identifying an amino acid residue to be excluded from an immunobinder, the method comprising:

a) providing a first database of grouped $V_H$ or $V_L$ amino acid sequences (e.g., germline and/or mature antibody sequences grouped according to Kabat family subtype);

b) providing a second database of grouped scFv antibody $V_H$ or $V_L$ amino acid sequences selected as having at least one desirable functional property (e.g., according to QC assay);

c) determining amino acid frequency for an amino acid residue at a framework position of the first database and at a corresponding framework position of the second database;

d) identifying the amino acid residue as a disfavored amino acid residue for substitution at corresponding amino acid position of the immunobinder when the amino acid residue occurs at a lower frequency in the second database relative to the first database, wherein said amino acid residue type is a disfavored amino acid residue (i.e., an excluded residue). In certain preferred embodiments, the disfavored amino acid residue in step (d) supra is identified if enrichment factor (EF) is less than 1.

Mutation of scFvs

In the methods of the invention, once one or more amino acid positions within a scFv have been identified as being potentially problematic with respect to the functional properties of the scFv, the method can further comprise mutating these one or more amino acid positions within the scFv $V_H$ or $V_L$ amino acid sequence. For example, an amino acid position identified for mutation can be substituted with an amino acid residue that is conserved at the corresponding position within the antibody $V_H$ or $V_L$ amino acid sequences of the database.

An amino acid position identified for mutation can be mutated using one of several possible mutagenesis methods well established in the art. For example, site directed mutagenesis can be used make a particular amino acid substitution at the amino acid position of interest. Site directed mutagenesis also can be used to create a set of mutated scFvs in which a limited repertoire of amino acid substitutions have been introduced at the amino acid position of interest.

Additionally or alternatively, the amino acid position identified for mutation can be mutated by random mutagenesis or by biased mutagenesis to generate a library of mutated scFvs, followed by screening of the library of mutated scFvs and selection of scFvs, preferably selection of scFvs having at least one improved functional property. In a preferred embodiment, the library is screened using a yeast Quality Control-system (QC-system) (described in further detail above), which allows for selection of scFv frameworks having enhanced stability and/or solubility in a reducing environment.

Other suitable selection technologies for screening scFv libraries have been described in the art, including but not limited to display technologies such as phage display, ribosome display and yeast display (Jung et al. (1999) *J. Mol. Biol.* 294: 163-180; Wu et al. (1999) *J. Mol. Biol.* 294: 151-162; Schier et al. (1996) *J. Mol. Biol.* 255: 28-43).

In one embodiment, an amino acid position identified for mutation is substituted with an amino acid residue that is most frequently at the corresponding position within the antibody $V_H$ or $V_L$ amino acid sequences of the database. In another embodiment, the corresponding position within the antibody $V_H$ or $V_L$ amino acid sequences of the database is conserved with hydrophobic amino acid residues and the amino acid position identified for mutation within the scFv is substituted with a hydrophobic amino acid residue that is most frequently at the corresponding position within the antibody $V_H$ or $V_L$ amino acid sequences of the database. In yet another embodiment, the corresponding position within the antibody $V_H$ or $V_L$ amino acid sequences of the database is conserved with hydrophilic amino acid residues and the amino acid position identified for mutation within the scFv is substituted with a hydrophilic amino acid residue that is most frequently at the corresponding position within the antibody $V_H$ or $V_L$ amino acid sequences of the database. In yet another embodiment, the corresponding position within the antibody $V_H$ or $V_L$ amino acid sequences of the database is conserved with amino acid residues capable of forming a hydrogen bond and the amino acid position identified for mutation within the scFv is substituted with an amino acid residue capable of forming a hydrogen bond that is most frequently at the corresponding position within the antibody $V_H$ or $V_L$ amino acid sequences of the database. In still another embodiment, the corresponding position within the antibody $V_H$ or $V_L$ amino acid sequences of the database is conserved with amino acid residues having a propensity to form a β-sheet and the amino acid position identified for mutation within the scFv is substituted with an amino acid residue having a propensity to form a β sheet that is most frequently at the corresponding position within the antibody $V_H$ or $V_L$ amino acid sequences of the database.

In one embodiment, the best substitution that minimizes the overall free energy is selected as the mutation to be made at the amino acid position(s) of interest. The best substitution that minimizes the overall free energy can be determined using Boltzmann's Law. The formula for Boltzmann's Law is $\Delta\Delta G_{th} = RT \ln(f_{parental}/f_{consensus})$.

The role of potentially stabilizing mutations can be further determined by examining, for example, local and non-local interactions, canonical residues, interfaces, exposure degree and β-turn propensity. Molecular modeling methods known in the art can be applied, for example, in further examining the role of potentially stabilizing mutations. Molecular modeling methods also can be used to select "best fit" amino acid substitutions if a panel of possible substitutions are under consideration.

Depending on the particular amino acid position, further analysis may be warranted. For example, residues may be involved in the interaction between the heavy and the light chain or may interact with other residues through salt bridges or H bonding. In these cases special analysis might be required. In another embodiment of present invention, a potentially problematic residue for stability can be changed to one that is compatible with its counterpart in a covariant pair. Alternatively, the counterpart residue can be mutated in order to be compatible with the amino acid initially identified as being problematic.

Solubility Optimization

Residues potentially problematic for solubility in a scFv antibody include hydrophobic amino acids that are exposed to solvent in a scFv and in natural state are buried at the interface between variable and constant domains. In an engineered scFv, which lacks the constant domains, hydrophobic residues that participated in the interactions between the variable and constant domains become solvent exposed (see e.g., Nieba et al. (1997) *Protein Eng.* 10: 435-44). These residues on the surface of the scFv tend to cause aggregation and therefore solubility problems.

A number of strategies have been described to replace hydrophobic amino acids that are exposed to solvent on scFv antibodies. As is well known by those skilled in the art, modifying residues at certain positions affects biophysical properties of antibodies like stability, solubility, and affinity. In many cases these properties are interrelated, which means that the change of one single amino acid can affect several of above-mentioned properties. Therefore, mutating hydrophobic residues exposed to the solvent in a non-conservative manner may cause decreased stability and/or loss in affinity for its antigen.

Other similar approaches, in most cases, intend to solve solubility problems by exhaustive use of protein display technologies and or screening efforts. However, such methods are time-consuming, often fail to yield soluble protein or result in lower stability or reduction of the affinity of the antibody. In the present invention, methods are disclosed to design mutations of solvent exposed hydrophobic residues to residues with a higher hydrophilicity using a sequence based analysis. The potentially problematic residues can be replaced by choosing the most frequently represented hydrophilic amino acid at defined positions. If a residue is found to interact with any other residue in the antibody, the potentially problematic residue can be mutated, not to the most frequent residue but to one that is compatible with the second amino acid of the covariant pair. Alternatively, a second amino acid of the covariant pair can also be mutated in order to restore the combination of amino acids. Furthermore, the percentage of similarity between sequences can be taken into account to assist finding of an optimal combination of two interrelated amino acids.

Hydrophobic amino acids on the surface of the scFv are identified using several approaches, including but not limited to approaches based on solvent exposure, experimental information and sequence information, as well as molecular modeling.

In one embodiment of this invention, the solubility is improved by replacing hydrophobic residues exposed on the surface of the scFv antibody with the most frequent hydrophilic residues present at these positions in databases. This rationale rests on the fact that frequently occurring residues are likely to be unproblematic. As will be appreciated by those skilled in the art, conservative substitutions usually have a small effect in destabilizing the molecule, whereas non-conservative substitutions might be detrimental for the functional properties of the scFv.

Sometimes hydrophobic residues on the surface of the antibody may be involved in the interaction between the heavy and the light chain or may interact with other residues through salt bridges or H bonding. In these cases special analysis might be required. In another embodiment of the present invention, the potentially problematic residues for solubility can be mutated not to the most frequent residue but to a compatible one with the covariant pair or a second mutation can be performed to restore the combination of co-variant amino acids.

Additional methods may be used to design mutations at solvent exposed hydrophobic positions. In another embodiment of this invention, methods are disclosed that employ constraining of the database to those sequences that reveal the highest similarity to the scFv to be modified (discussed further above). By applying such a constrained reference database, the mutation is designed such that it best fits in the specific sequence context of the antibody to be optimized. In this situation, the chosen hydrophilic residue may in fact be poorly represented at its respective position when compared to a larger number of sequences (i.e., the unconstrained database).

Stability Optimization

Single-chain antibody fragments contain a peptide linker that covalently joins the light and heavy variable domains. Although such a linker is effective to avoid having the variable domains come apart, and thereby makes the scFv superior over the Fv fragment, the scFv fragment still is more prone to unfolding and aggregation as compared to an Fab fragment or to a full-length antibody, in both of which the $V_H$ and the $V_L$ are only linked indirectly via the constant domains.

Another common problem in scFvs is exposure of hydrophobic residues on the surface of the scFv that lead to intermolecular aggregation. Furthermore, sometimes somatic mutations acquired during the process of affinity maturation place hydrophilic residues in the core of the β-sheet. Such mutations may be well tolerated in the IgG format or even in a Fab fragment but in an scFv this clearly contributes to destabilization and consequent unfolding.

Known factors that contribute to scFv destabilization include: solvent exposed hydrophobic residues on the surface of the scFv antibody; unusual hydrophilic residues buried in the core of the protein, as well as hydrophilic residues present in the hydrophobic interface between the heavy and the light chains. Furthermore, van der Waals packing interactions between nonpolar residues in the core are known to play an important role in protein stability (Monsellier E. and Bedouelle H. (2006) *J. Mol. Biol.* 362: 580-93, Tan et al. (1998) *Biophys. J.* 75:1473-82; Worn A. and Pluckthun A. (1998) *Biochemistry* 37:13120-7).

Thus, in one embodiment, in order to increase the stability of scFv antibodies, unusual and/or unfavorable amino acids at very conserved positions are identified and mutated to amino acids that are more common at these conserved positions. Such unusual and/or unfavorable amino acids include: (i) solvent exposed hydrophobic residues on the surface of the scFv antibody; (ii) unusual hydrophilic residues buried in the core of the protein; and (iii) hydrophilic residues present in the hydrophobic interface between the heavy and the light chains.

Thus, in one embodiment of this invention, an increase in stability can be achieved by substituting amino acids that are poorly represented at their positions by amino acids that occur most frequently at these positions. Frequency of occurrence generally provides an indication of biological acceptance.

Residues may be involved in the interaction between the heavy and the light chain or may interact with other residues through salt bridges or H bonding. In these cases special analysis might be required. In another embodiment of present invention, a potentially problematic residue for stability can be changed to one that is compatible with its counterpart in a covariant pair. Alternatively, the counterpart residue can be mutated in order to be compatible with the amino acid initially identified as being problematic.

Additional methods may be used to design mutations to improve stability. In another embodiment of this invention, methods are disclosed that employ constraining of the database to those sequences that reveal the highest similarity to the scFv to be modified (discussed further above). By applying such a constrained reference database, the mutation is designed such that it best fits in the specific sequence context of the antibody to be optimized. The mutation uses the most frequent amino acid that is present in the selected subset of database sequences. In this situation, the chosen residue may in fact be poorly represented at its respective position when compared to a larger number of sequences (i.e., the unconstrained database).

ScFv Compositions and Formulations

Another aspect of the invention pertains to scFv composition prepared according to the methods of invention. Thus, the invention provides engineered scFv compositions in which one or more mutations have been introduced into the amino acid sequence, as compared to an original scFv of interest, wherein the mutation(s) has been introduced into a position(s) predicted to influence one or more biological properties, such as stability or solubility, in particular one or more framework positions. In one embodiment, the scFv has been engineered to contain one mutated amino acid position (e.g., one framework position). In other embodiments, the scFv has been engineered to contain two, three, four, five, six, seven, eight, nine, ten or more than ten mutated amino acid positions (e.g., framework positions).

Another aspect of the invention pertains to pharmaceutical formulations of the scFv compositions of the invention. Such formulations typically comprise the scFv composition and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for, for example, intravenous, intramuscular, subcutaneous, parenteral, spinal or epidermal administration (e.g., by injection or infusion). Depending on the route of administration, the scFv may be coated in a material to protect the compound from the action of acids and other natural conditions that may inactivate the compound.

The pharmaceutical compounds of the invention may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the invention also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

Immunobinder Engineering Based on "Functional Consensus" Approach

As described in detail in Examples 2 and 3, the "functional consensus" approach described herein, in which a database of scFv sequences selected for improved properties is used to analyze framework position variability, allows for the identification of amino acid positions that are either more or less tolerant of variability as compared to variability at these same positions in germline and/or mature antibody databases. As described in detail in Examples 5 and 6, back-mutation of certain amino acid positions within a sample scFv to the germline consensus residue has either a neutral or detrimental effect, whereas scFv variants that contain "functional consensus" residues exhibit increased thermal stability as compared to the wild-type scFv molecule. Accordingly, the framework positions identified herein through the functional consensus approach are preferred positions for scFv modification in order to alter, and preferably improve, the functional properties of the scFv. As set forth in Table 3-8 in Example 3, the following framework positions have been identified as preferred positions for modification in the indicated $V_H$ or $V_L$ sequences (the numbering used below is the AHo numbering system; conversion tables to convert the AHo numbering to the Kabat system numbering are set forth as Tables 1 and 2 in Example 1):

VH3: amino acid positions 1, 6, 7, 89 and 103;

VH1a: amino acid positions 1, 6, 12, 13, 14, 19, 21, 90, 92, 95 and 98;

VH1b: amino acid positions 1, 10, 12, 13, 14, 20, 21, 45, 47, 50, 55, 77, 78, 82, 86, 87 and 107;

Vκ1: amino acid positions 1, 3, 4, 24, 47, 50, 57, 91, and 103;

Vκ3: 2, 3, 10, 12, 18, 20, 56, 74, 94, 101 and 103; and

Vλ1: 1, 2, 4, 7, 11, 14, 46, 53, 82, 92 and 103.

Accordingly, one or more of these amino acid positions can be selected for engineering in immunobinders, such as scFv molecules, to thereby produce variant (i.e., mutated) forms of the immunobinders. Thus, in yet another aspect, the invention provides a method of engineering an immunobinder, the method comprising:

a) selecting one or more amino acid positions within the immunobinder for mutation; and b) mutating the one more amino acid positions selected for mutation, wherein the one or more amino acid positions selected for mutation are selected from the group consisting of:

(i) amino acid positions 1, 6, 7, 89 and 103 of VH3 using AHo numbering (amino acid positions 1, 6, 7, 78 and 89 using Kabat numbering);

(ii) amino acid positions 1, 6, 12, 13, 14, 19, 21, 90, 92, 95 and 98 of VH1a using AHo numbering (amino acid positions 1, 6, 11, 12, 13, 18, 20, 79, 81, 82b and 84 using Kabat numbering);

(iii) amino acid positions 1, 10, 12, 13, 14, 20, 21, 45, 47, 50, 55, 77, 78, 82, 86, 87 and 107 of VH1b using AHo numbering (amino acid positions 1, 9, 11, 12, 13, 19, 20, 38, 40, 43, 48, 66, 67, 71, 75, 76 and 93 using Kabat numbering);

(iv) amino acid positions 1, 3, 4, 24, 47, 50, 57, 91 and 103 of Vκ1 using AHo numbering (amino acid positions 1, 3, 4, 24, 39, 42, 49, 73, and 85 using Kabat numbering);

(v) amino acid positions 2, 3, 10, 12, 18, 20, 56, 74, 94, 101 and 103 of Vκ3 using AHo numbering (amino acid positions 2, 3, 10, 12, 18, 20, 48, 58, 76, 83 and 85 using Kabat numbering); and (vi) amino acid positions 1, 2, 4, 7, 11, 14, 46, 53, 82, 92 and 103 of Vλ1 using AHo numbering (amino acid positions 1, 2, 4, 7, 11, 14, 38, 45, 66, 74 and 85 using Kabat numbering).

In a preferred embodiment, the one or more amino acid positions selected for mutation are selected from the group consisting of amino acid positions 1, 6, 7, 89 and 103 of VH3 using AHo numbering (amino acid positions 1, 6, 7, 78 and 89 using Kabat numbering).

In another preferred embodiment, the one or more amino acid positions selected for mutation are selected from the group consisting of amino acid positions 1, 6, 12, 13, 14, 19, 21, 90, 92, 95 and 98 of VH1a using AHo numbering (amino acid positions 1, 6, 11, 12, 13, 18, 20, 79, 81, 82b and 84 using Kabat numbering).

In another preferred embodiment, the one or more amino acid positions selected for mutation are selected from the group consisting of amino acid positions 1, 10, 12, 13, 14, 20, 21, 45, 47, 50, 55, 77, 78, 82, 86, 87 and 107 of VH1b using AHo numbering (amino acid positions 1, 9, 11, 12, 13, 19, 20, 38, 40, 43, 48, 66, 67, 71, 75, 76 and 93 using Kabat numbering).

In another preferred embodiment, the one or more amino acid positions selected for mutation are selected from the group consisting of amino acid positions 1, 3, 4, 24, 47, 50, 57, 91 and 103 of Vκ1 using AHo numbering (amino acid positions 1, 3, 4, 24, 39, 42, 49, 73 and 85 using Kabat numbering).

In another preferred embodiment, the one or more amino acid positions selected for mutation are selected from the group consisting of amino acid positions 2, 3, 10, 12, 18, 20, 56, 74, 94, 101 and 103 of Vκ3 using AHo numbering (amino acid positions 2, 3, 10, 12, 18, 20, 48, 58, 76, 83 and 85 using Kabat numbering).

In another preferred embodiment, one or more amino acid positions selected for mutation are selected from the group consisting of amino acid positions 1, 2, 4, 7, 11, 14, 46, 53, 82, 92 and 103 of Vλ1 using AHo numbering (amino acid positions 1, 2, 4, 7, 11, 14, 38, 45, 66, 74 and 85 using Kabat numbering).

In various embodiments, one, two, three, four, five, six, seven, eight, nine, ten, eleven, twelve, thirteen, fourteen, fifteen, sixteen, seventeen, eighteen, nineteen, twenty or more than twenty of the above-described amino acid positions are selected for mutation.

Preferably, the immunobinder is a scFv, but other immunobinders, such as full-length immunoglobins, Fab fragments or any other type of immunobinder described herein, also can be engineered according to the method. The invention also encompasses immunobinders prepared according to the engineering method, as well as compositions comprising the immunobinders and a pharmaceutically acceptable carrier.

Nothwithstanding the foregoing, in various embodiments, certain immunobinders are excluded from being used in the engineering methods of the invention and/or are excluded from being the immunobinder composition produced by the engineering methods. For example, in various embodiments, there is a proviso that the immunobinder is not any of the scFv antibodies, or variants thereof, as disclosed in PCT Publications WO 2006/131013 and WO 2008/006235, such as ESBA105 or variants thereof that are disclosed in PCT Publications WO 2006/131013 and WO 2008/006235, the contents of each of which is expressly incorporated herein by reference.

In various other embodiments, if the immunobinder to be engineered according to the above-described methods is any of the scFv antibodies, or variants thereof, disclosed in PCT publications WO 2006/131013 or WO 2008/006235, then there can be the proviso that the list of possible amino acid positions that may be selected for substitution according to the engineering method does not include any or all of the following amino acid positions: AHo position 4 (Kabat 4) of Vκ1 or Vλ1; AHo position 101 (Kabat 83) of Vκ3; AHo position 12 (Kabat 11) of VH1a or VH1b; AHo position 50 (Kabat 43) of VH1b; AHo position 77 (Kabat 66) for VH1b; AHo position 78 (Kabat 67) for VH1b; AHo position 82 (Kabat 71) for VH1b; AHo position 86 (Kabat 75) for VH1b; AHo position 87 (Kabat 76) for VH1b; AHo position 89 (Kabat 78) for VH3; AHo position 90 (Kabat 79) for VH1a; and/or AHo position 107 (Kabat 93) for VH1b.

In still various other embodiments, for any immunobinder to be engineered according to the above-described methods, and/or any immunobinder produced according to the above-described methods, there can be the proviso that the list of possible amino acid positions that may be selected for substitution according to the engineering method does not include any or all of the following amino acid positions: AHo position 4 (Kabat 4) of Vκ1 or Vλ1; AHo position 101 (Kabat 83) of Vκ3; AHo position 12 (Kabat 11) of VH1a or VH1b; AHo position 50 (Kabat 43) of VH1b; AHo position 77 (Kabat 66) for VH1b; AHo position 78 (Kabat 67) for VH1b; AHo position 82 (Kabat 71) for VH1b; AHo position 86 (Kabat 75) for VH1b; AHo position 87 (Kabat 76) for VH1b; AHo position 89 (Kabat 78) for VH3; AHo position 90 (Kabat 79) for VH1a; and/or AHo position 107 (Kabat 93) for VH1b.

Other Embodiments

It is understood that the invention also includes any of the methodologies, references, and/or compositions set forth in Appendices (A-C) of U.S. Provisional Patent Application Ser. No. 60/905,365, including, but not limited to, identified databases, bioinformatics, in silico data manipulation and interpretation methods, functional assays, preferred sequences, preferred residue(s) positions/alterations, framework identification and selection, framework alterations, CDR alignment and integration, and preferred alterations/mutations.

Additional information regarding these methodologies and compositions can be found in U.S. Ser. Nos. 60/819,378; and 60/899,907, and PCT Publication WO 2008/006235, entitled "scFv Antibodies Which Pass Epithelial And/Or Endothelial Layers" filed in July, 2006 and Feb. 6, 2007 respectively; WO06131013A2 entitled "Stable And Soluble Antibodies Inhibiting TNFα" filed Jun. 6, 2006; EP1506236A2 entitled "Immunoglobulin Frameworks Which Demonstrate Enhanced Stability In The Intracellular Environment And Methods Of Identifying Same" filed May 21, 2003; EP1479694A2 entitled "Intrabodies ScFv with defined framework that is stable in a reducing environment" filed Dec. 18, 2000; EP1242457B1 entitled "Intrabodies With Defined Framework That Is Stable In A Reducing Environment And Applications Thereof" filed Dec. 18, 2000; WO03097697A2 entitled "Immunoglobulin Frameworks Which Demonstrate Enhanced Stability In The Intracellular Environment And Methods Of Identifying Same" filed May 21, 2003; and WO0148017A1 entitled "Intrabodies With Defined Framework That Is Stable In A Reducing Environment And Applications Thereof" filed Dec. 18, 2000; and Honegger et al., J. Mol. Biol. 309:657-670 (2001).

Further, it is understood that the invention also includes methodologies and compositions suitable for the discovery and/or improvement of other antibody formats, e.g., full length antibodies or fragments thereof, for example Fabs, Dabs, and the like. Accordingly, the principles and residues identified herein as suitable for selection or alteration to achieve desired biophysical and/or therapeutic proprieties that can be applied to a wide range of immunobinders. In one embodiment, therapeutically relevant antibodies, for example, FDA-approved antibodies, are improved by modifying one or more residue positions as disclosed herein.

The present disclosure is further illustrated by the following examples, which should not be construed as further limiting. The contents of all figures and all references, patents and published patent applications cited throughout this application are expressly incorporated herein by reference in their entireties.

Example 1: Antibody Position Numbering Systems

In this example, conversion tables are provided for two different numbering systems used to identify amino acid residue positions in antibody heavy and light chain variable regions. The Kabat numbering system is described further in Kabat et al. (Kabat, E. A., et al. (1991) Sequences of Proteins of Immunological Interest, Fifth Edition, U.S. Department of Health and Human Services, NIH Publication No. 91-3242). The AHo numbering system is described further in Honegger, A. and Pluckthun, A. (2001) *J. Mol. Biol.* 309:657-670).

Heavy Chain Variable Region Numbering

TABLE 1

Conversion table for the residue positions in the Heavy Chain Variable Domain

| Kabat | AHo | Kabat | AHo | Kabat | AHo |
|---|---|---|---|---|---|
| 1 | 1 | 44 | 51 | 87 | 101 |
| 2 | 2 | 45 | 52 | 88 | 102 |
| 3 | 3 | 46 | 53 | 89 | 103 |
| 4 | 4 | 47 | 54 | 90 | 104 |
| 5 | 5 | 48 | 55 | 91 | 105 |
| 6 | 6 | 49 | 56 | 92 | 106 |
| 7 | 7 | 50 | 57 | 93 | 107 |
| * | 8 | 51 | 58 | 94 | 108 |
| 8 | 9 | 52 | 59 | 95 | 109 |
| 9 | 10 | 52a | 60 | 96 | 110 |
| 10 | 11 | 52b | 61 | 97 | 111 |
| 11 | 12 | 52c | 62 | 98 | 112 |

TABLE 1-continued

Conversion table for the residue positions in the Heavy Chain Variable Domain

| Kabat | AHo | Kabat | AHo | Kabat | AHo |
|---|---|---|---|---|---|
| 12 | 13 | * | 63 | 99 | 113 |
| 13 | 14 | 53 | 64 | 100 | 114 |
| 14 | 15 | 54 | 65 | 100a | 115 |
| 15 | 16 | 55 | 66 | 100b | 116 |
| 16 | 17 | 56 | 67 | 100c | 117 |
| 17 | 18 | 57 | 68 | 100d | 118 |
| 18 | 19 | 58 | 69 | 100e | 119 |
| 19 | 20 | 59 | 70 | 100f | 120 |
| 20 | 21 | 60 | 71 | 100g | 121 |
| 21 | 22 | 61 | 72 | 100h | 122 |
| 22 | 23 | 62 | 73 | 100i | 123 |
| 23 | 24 | 63 | 74 | * | 124 |
| 24 | 25 | 64 | 75 | * | 125 |
| 25 | 26 | 65 | 76 | * | 126 |
| 26 | 27 | 66 | 77 | * | 127 |
| * | 28 | 67 | 78 | * | 128 |
| 27 | 29 | 68 | 79 | * | 129 |
| 28 | 30 | 69 | 80 | * | 130 |
| 29 | 31 | 70 | 81 | * | 131 |
| 30 | 32 | 71 | 82 | * | 132 |
| 31 | 33 | 72 | 83 | * | 133 |
| 32 | 34 | 73 | 84 | * | 134 |
| 33 | 35 | 74 | 85 | * | 135 |
| 34 | 36 | 75 | 86 | * | 136 |
| 35 | 37 | 76 | 87 | 101 | 137 |
| 35a | 38 | 77 | 88 | 102 | 138 |
| 35b | 39 | 78 | 89 | 103 | 139 |
| * | 40 | 79 | 90 | 104 | 140 |
| * | 41 | 80 | 91 | 105 | 141 |
| * | 42 | 81 | 92 | 106 | 142 |
| 36 | 43 | 82 | 93 | 107 | 143 |
| 37 | 44 | 82a | 94 | 108 | 144 |
| 38 | 45 | 82b | 95 | 109 | 145 |
| 39 | 46 | 82b | 96 | 110 | 146 |
| 40 | 47 | 83 | 97 | 111 | 147 |
| 41 | 48 | 84 | 98 | 112 | 148 |
| 42 | 49 | 85 | 99 | 113 | 149 |
| 43 | 50 | 86 | 100 | | |

Column 1, Residue position in Kabat's numbering system.
Column 2, Corresponding number in AHo's numbering system for the position indicated in column 1.
Column 3, Residue position in Kabat's numbering system.
Column 4, Corresponding number in AHo's numbering system for the position indicated in column 3.
Column 5, Residue position in Kabat's numbering system.
Column 6, Corresponding number in AHo's numbering system for the position indicated in column 5

Light Chain Variable Region Numbering

TABLE 2

Conversion table for the residue positions in the Light Chain Variable Domain

| Kabat | AHo | Kabat | AHo | Kabat | AHo |
|---|---|---|---|---|---|
| 1 | 1 | 43 | 51 | 83 | 101 |
| 2 | 2 | 44 | 52 | 84 | 102 |
| 3 | 3 | 45 | 53 | 85 | 103 |
| 4 | 4 | 46 | 54 | 86 | 104 |
| 5 | 5 | 47 | 55 | 87 | 105 |
| 6 | 6 | 48 | 56 | 88 | 106 |
| 7 | 7 | 49 | 57 | 89 | 107 |
| 8 | 8 | 50 | 58 | 90 | 108 |
| 9 | 9 | * | 59 | 91 | 109 |
| 10 | 10 | * | 60 | 92 | 110 |
| 11 | 11 | * | 61 | 93 | 111 |
| 12 | 12 | * | 62 | 94 | 112 |
| 13 | 13 | * | 63 | 95 | 113 |
| 14 | 14 | * | 64 | 95a | 114 |
| 15 | 15 | * | 65 | 95b | 115 |
| 16 | 16 | * | 66 | 95c | 116 |
| 17 | 17 | 51 | 67 | 95d | 117 |
| 18 | 18 | 52 | 68 | 95e | 118 |

TABLE 2-continued

Conversion table for the residue positions in the Light Chain Variable Domain

| Kabat | AHo | Kabat | AHo | Kabat | AHo |
|---|---|---|---|---|---|
| 19 | 19 | 53 | 69 | 95f | 119 |
| 20 | 20 | 54 | 70 | * | 120 |
| 21 | 21 | 55 | 71 | * | 121 |
| 22 | 22 | 56 | 72 | * | 122 |
| 23 | 23 | 57 | 73 | * | 123 |
| 24 | 24 | 58 | 74 | * | 124 |
| 25 | 25 | 59 | 75 | * | 125 |
| 26 | 26 | 60 | 76 | * | 126 |
| 27 | 27 | 61 | 77 | * | 127 |
| * | 28 | 62 | 78 | * | 128 |
| 27a | 29 | 63 | 79 | * | 129 |
| 27b | 30 | 64 | 80 | * | 130 |
| 27c | 31 | 65 | 81 | * | 131 |
| 27d | 32 | 66 | 82 | * | 132 |
| 27e | 33 | 67 | 83 | * | 133 |
| 27f | 34 | 68 | 84 | * | 134 |
| * | 35 | * | 85 | * | 135 |
| 28 | 36 | * | 86 | * | 136 |
| 29 | 37 | 69 | 87 | 96 | 137 |
| 30 | 38 | 70 | 88 | 97 | 138 |
| 31 | 39 | 71 | 89 | 98 | 139 |
| 32 | 40 | 72 | 90 | 99 | 140 |
| 33 | 41 | 73 | 91 | 100 | 141 |
| 34 | 42 | 74 | 92 | 101 | 142 |
| 35 | 43 | 75 | 93 | 102 | 143 |
| 36 | 44 | 76 | 94 | 103 | 144 |
| 37 | 45 | 77 | 95 | 104 | 145 |
| 38 | 46 | 78 | 96 | 105 | 146 |
| 39 | 47 | 79 | 97 | 106 | 147 |
| 40 | 48 | 80 | 98 | 107 | 148 |
| 41 | 49 | 81 | 99 | 108 | 149 |
| 42 | 50 | 82 | 100 | | |

Column 1, Residue position in Kabat's numbering system.
Column 2, Corresponding number in AHo's numbering system for the position indicated in column 1.
Column 3, Residue position in Kabat's numbering system.
Column 4, Corresponding number in AHo's numbering system for the position indicated in column 3.
Column 5, Residue position in Kabat's numbering system.
Column 6, Corresponding number in AHo's numbering system for the position indicated in column 5

Example 2: Sequence-Based Analysis of scFv Sequences

In this example, the sequence-based analysis of scFv sequences is described in detail. A flowchart summarizing the process of the analysis is shown in FIG. 1.

Collection and Alignment of Human Immunoglobulin Sequences

Sequences of variable domains of human mature antibodies and germlines were collected from different databases and entered into a customized database as one letter code amino acid sequences. The antibody sequences were aligned using an EXCEL implementation of the Needleman-Wunsch sequence alignment algorithm (Needleman et al., J Mol Biol, 48(3):443-53 (1970)). The database was then subdivided into four different arrays (according to the original data source) to facilitate the subsequent analysis and comparison, as follows:
 VBase: Human germline sequences
 IMGT: Human germline sequences
 KDB database: Mature antibodies
 QC database: Selected scFv frameworks selected by Quality Control screening The QC screening system, and scFv framework sequences having desirable functional properties selected therefrom, are described further in, for example, PCT Publication WO 2001/48017; U.S. Application No. 20010024831; US 20030096306; U.S. Pat. Nos. 7,258,985 and 7,258,986; PCT Publication WO 2003/097697 and U.S. Application No. 20060035320.

The introduction of gaps and the nomenclature of residue positions were done following AHo's numbering system for immunoglobulin variable domain (Honegger, A. and Pluckthun, A. (2001) *J. Mol. Biol.* 309:657-670). Subsequently, framework regions and CDRs regions were identified according to Kabat et al. (Kabat, E. A., et al. (1991) Sequences of Proteins of Immunological Interest, Fifth Edition, U.S. Department of Health and Human Services, NIH Publication No. 91-3242). Sequences in the KDB database less than 70% complete or containing multiple undetermined residues in the framework regions were discarded. Sequences with more than 95% identity to any other sequence within the database were also excluded to avoid random noise in the analysis.

Assignment of Sequences to Subgroups

The antibody sequences were classified into distinct families by clustering the antibodies according to classification methods based on sequence homology (Tomlinson, I. M. et al. (1992) *J. Mol. Biol.* 227:776-798; Williams, S. C. and Winter, G. (1993) *Eur. J. Immunol.* 23:1456-1461); Cox, J. P. et al. (1994) *Eur. J. Immunol.* 24:827-836). The percentage of homology to the family consensus was constrained to 70% similarity. In cases where sequences showed conflicts between two or more different germline families, or the percentage of homology was below 70% (to any family), the nearest germline counterpart was determined, CDRs length, canonical classes and defining subtype residues were analyzed in detail to correctly assign the family.

Statistical Analysis

Once the family clusters were defined, statistical analysis were performed for hits identified in the "Quality Control ("QC") screening" (such QC screening is described in detail in PCT Publication WO 2003/097697). Analyses were only possible for the most represented families (VH3, VH1a, VH1b, Vk1, Vk3 and Vλ1) since a minimum number of sequences are needed for the analysis. The residue frequencies, fi(r), for each position, i, was calculated by the number of times that particular residue-type was observed within the data set divided by the total number of sequences. The positional entropy, N(i), was calculated as a measure of every residue position's variability (Shenkin, P. S. et al. (1991) *Proteins* 11:297-313; Larson, S. M. and Davidson, A. R. (2000) *Protein Sci.* 9:2170-2180; Demarest, S. J. et al. (2004) *J. Mol. Biol.* 335:41-48) using the Simpson's index which is a mathematical measure of diversity in a system providing more information about amino acids composition than simply richness. The degree of diversity for each position, i, was calculated taking into account the number of different amino acids present, as well as the relative abundance of each residue.

$$D = \frac{\sum_{i=1}^{r} n(n-1)}{N(N-1)}$$

Where: D is the Simpson's Index, N is the total number of amino acids, r is the number of different amino acids present at each position and n is the number of residues of a particular amino acid type.

The QC database of the selected Fv frameworks (selected by the QC screening) was screened using different criteria to define the unique features. The different arrays in the sequence database were used to define the degree of variability of residue positions within the Fv frameworks and to identify variation-tolerant positions not common in nature which are present in the selected Fv frameworks. A difference in the positional entropy scores equal or more than 10% was defined as a threshold. Additional positions were selected if the residue at a given position was occupied by an amino acid infrequently observed in the other sequence arrays, i.e., infrequently observed in the germlines databases (VBase and IMGT) and the KDB database. If the behavior of a residue was found to be truly different, (low or none represented in any of the other sequence arrays), the residue position was defined as unique.

The rationale behind the identification of unique features of the selected Fv framework sequences is the proven superior properties of the frameworks and the potential use of these findings for improved scaffolding. We assumed that highly conserved positions in nature showing a certain degree of variability in the selected frameworks should tolerate random mutagenesis and present an increased probability of finding alternative amino acids superior to the native residue in a scFv format. In addition a pronounced preference for an uncommon amino acid is an indication of natural selection toward certain residue. Based on these two statistical guidelines different residues within the heavy and light chains were chosen as either floating positions (variability-tolerant) or preferred substitutions (unusual residues).

Example 3: Identification of Variability-Tolerant and Unusual Residue Positions Using the sequence-based scFv analysis approach described above in Example 2, three heavy chain variable region families (VH3, VH1a and VH1b) and three light chain variable region families (Vκ1, Vκ3 and Vλ1) were analyzed to identify variability-tolerant amino acid positions. In particular, the degree of diversity, as calculated using the Simpson's Index, was determined for each amino acid position for sequences within four different databases, Vbase, IMGT, KDB and QC (selected scFvs), as described above. Variant-tolerant and unusual residue amino acid positions were identified based on differences in the Simpson's Index values at those positions for the Vbase and IMGT germline databases as compared to the QC selected scFv database. Additionally, for the identified positions of interest, the germline consensus residue was identified and the frequency of that consensus residue in the QC and KDB databases was determined.

The variability analysis results for the heavy chain variable region families VH3, VH1a and VH1b are shown below in Tables 3, 4 and 5, respectively. For each table, the columns are as follows: column 1: amino acid residue position using the AHo numbering system (conversion to the Kabat numbering system can be accomplished using the conversion table set forth as Table 1 in Example 1); columns 2 to 5: calculated diversity for each antibody array in the database for the residue position indicated in column 1; column 6: consensus residue of the corresponding germline family and KDB; column 7: relative residue frequency in the KDB database for the consensus residue in column 6; and column 8: relative residue frequency in the QC selected scFv database for the consensus residue in column 6.

TABLE 3

Variability analysis of residues and corresponding frequencies of the consensus amino acid identified in the germline for the VH3 family.

| Residue position | IMGT germline | VBase germline | QC selected scFv | KDBseq | Consensus residue | f (cons KDB) | f (cons QC) |
|---|---|---|---|---|---|---|---|
| 1 | 0.68 | 0.65 | 0.50 | 0.53 | E | 66.67 | 53.57 |
| 6 | 1.00 | 1.00 | 0.57 | 0.86 | E | 92.56 | 68.97 |
| 7 | 1.00 | 0.91 | 0.65 | 0.93 | S | 96.33 | 77.59 |
| 89 | 0.86 | 0.83 | 0.55 | 0.71 | L | 84.06 | 70.18 |
| 103 | 0.73 | 0.76 | 0.38 | 0.76 | V | 86.85 | 55.36 |

TABLE 4

Variability analysis of residues and corresponding frequencies of the consensus amino acid identified in the germline for the VH1a family.

| Residue position | IMGT germline | VBase germline | QC selected scFv | KDBseq | Consensus residue | f (cons KDB) | f (cons QC) |
|---|---|---|---|---|---|---|---|
| 1 | 0.82 | 0.83 | 0.62 | 0.77 | Q | 86.60 | 75.00 |
| 6 | 1.00 | 1.00 | 0.51 | 0.74 | Q | 84.31 | 58.30 |
| 12 | 1.00 | 1.00 | 0.72 | 0.93 | V | 96.29 | 83.30 |
| 13 | 1.00 | 1.00 | 0.72 | 0.86 | K | 92.59 | 83.30 |
| 14 | 1.00 | 1.00 | 0.60 | 0.93 | K | 96.29 | 75.00 |
| 19 | 1.00 | 1.00 | 0.72 | 1.00 | V | 100.00 | 83.30 |
| 21 | 0.83 | 0.83 | 0.72 | 0.96 | V | 98.14 | 83.30 |
| 90 | 1.00 | 1.00 | 0.47 | 0.89 | Y | 94.44 | 66.60 |
| 92 | 0.83 | 1.00 | 0.60 | 0.93 | E | 96.29 | 75.00 |
| 95 | 0.83 | 0.83 | 0.49 | 0.70 | S | 83.33 | 66.60 |
| 98 | 1.00 | 1.00 | 0.39 | 0.83 | S | 90.74 | 38.30 |

TABLE 5

Variability analysis of residues and corresponding frequencies of the consensus amino acid identified in the germline for the VH1b family.

| Residue position | IMGT germline | VBase germline | QC selected scFv | KDBseq | Consensus residue | f (cons KDB) | f (cons QC) |
|---|---|---|---|---|---|---|---|
| 1 | 0.82 | 0.83 | 0.58 | 0.92 | Q | 95.65 | 70.59 |
| 10 | 0.82 | 0.83 | 0.52 | 0.73 | A | 85.00 | 70.59 |
| 12 | 1.00 | 1.00 | 0.64 | 0.86 | V | 92.59 | 76.47 |
| 13 | 1.00 | 1.00 | 0.52 | 0.86 | K | 92.59 | 70.59 |
| 14 | 1.00 | 1.00 | 0.54 | 0.88 | K | 93.83 | 70.59 |
| 20 | 1.00 | 1.00 | 0.61 | 0.86 | K | 92.59 | 76.47 |
| 21 | 0.83 | 0.83 | 0.47 | 0.84 | V | 91.36 | 64.71 |
| 45 | 0.70 | 0.83 | 0.64 | 0.90 | R | 95.06 | 76.47 |
| 47 | 0.83 | 1.00 | 0.31 | 0.95 | A | 97.53 | 47.06 |
| 50 | 0.70 | 0.70 | 0.48 | 0.76 | Q | 86.42 | 64.71 |
| 55 | 0.83 | 0.83 | 0.64 | 0.82 | M | 90.12 | 76.47 |
| 77 | 1.00 | 1.00 | 0.64 | 1.00 | R | 100.00 | 76.47 |
| 78 | 0.83 | 1.00 | 0.32 | 0.76 | A | 86.42 | 47.06 |
| 82 | 0.45 | 0.39 | 0.25 | 0.36 | R | 55.56 | 29.41 |
| 86 | 0.45 | 0.45 | 0.37 | 0.27 | I | 24.69 | 17.65 |
| 87 | 0.57 | 0.70 | 0.30 | 0.53 | S | 70.37 | 25.00 |
| 107 | 1.00 | 1.00 | 0.60 | 0.90 | A | 95.00 | 75.00 |

The variability analysis results for the light chain variable region families Vκ1, Vκ3 and Vλ1 are shown below in Tables 6, 7 and 8, respectively. For each table, the columns are as follows: column 1: amino acid residue position using the AHo numbering system (conversion to the Kabat numbering system can be accomplished using the conversion table set forth as Table 1 in Example 1); columns 2 to 5: calculated diversity for each antibody array in the database for the residue position indicated in column 1; column 6: consensus residue of the corresponding germline family and KDB; column 7: relative residue frequency in the KDB database for the consensus residue in column 6; and column 8: relative residue frequency in the QC selected scFv database for the consensus residue in column 6.

TABLE 6

Variability analysis of residues and corresponding frequencies of the consensus amino acid identified in the germline for the Vk1 family.

| Residue position | IMGT germline | VBase germline | QC selected scFv | KDBseq | Consensus residue | f (cons KDB) | f (cons QC) |
|---|---|---|---|---|---|---|---|
| 1 | 0.52 | 0.47 | 0.61 | 0.68 | D | 81.5 | 23.3 |
| 3 | 0.76 | 0.72 | 0.66 | 0.55 | Q | 72.0 | 18.6 |
| 4 | 0.65 | 0.73 | 0.57 | 0.62 | M | 76.0 | 23.3 |
| 24 | 0.69 | 0.72 | 0.64 | 0.74 | R | 85.3 | 76.7 |
| 47 | 1.00 | 1.00 | 0.69 | 0.88 | K | 94.0 | 81.4 |
| 50 | 1.00 | 1.00 | 0.60 | 0.79 | R | 89.0 | 76.7 |
| 57 | 1.00 | 1.00 | 0.58 | 0.79 | Y | 88.6 | 74.4 |
| 91 | 0.83 | 0.81 | 0.70 | 0.77 | L | 86.6 | 81.4 |
| 103 | 0.91 | 1.00 | 0.67 | 0.90 | T | 81.4 | 95.7 |

TABLE 7

Variability analysis of residues and corresponding frequencies of the consensus amino acid identified in the germline for the Vk3 family.

| Residue position | IMGT germline | VBase germline | QC selected scFv | KDBseq | Consensus residue | f (cons KDB) | f (cons QC) |
|---|---|---|---|---|---|---|---|
| 2 | 1.00 | 1.00 | 0.72 | 0.69 | I | 82.47 | 83.33 |
| 3 | 1.00 | 1.00 | 0.72 | 0.64 | V | 77.93 | 83.33 |
| 10 | 1.00 | 1.00 | 0.72 | 0.93 | T | 96.19 | 83.33 |
| 12 | 1.00 | 1.00 | 0.72 | 0.98 | S | 98.84 | 83.33 |
| 18 | 1.00 | 1.00 | 0.72 | 0.92 | R | 95.86 | 83.33 |
| 20 | 1.00 | 1.00 | 0.68 | 0.95 | T | 97.30 | 66.67 |
| 56 | 1.00 | 1.00 | 0.72 | 0.91 | I | 95.31 | 83.33 |
| 74 | 1.00 | 1.00 | 0.50 | 0.86 | I | 92.61 | 66.67 |
| 94 | 1.00 | 1.00 | 0.72 | 0.82 | S | 90.29 | 83.33 |
| 101 | 1.00 | 1.00 | 0.50 | 0.91 | F | 95.14 | 66.67 |
| 103 | 1.00 | 1.00 | 0.50 | 0.82 | F | 90.47 | 66.67 |

TABLE 8

Variability analysis of residues and corresponding frequencies of the consensus amino acid identified in the germline for the Vλ1 family.

| Residue position | IMGT germline | VBase germline | QC selected scFv | KDBseq | Consensus residue | f (cons KDB) | f (cons QC) |
|---|---|---|---|---|---|---|---|
| 1 | 1.00 | 1.00 | 0.45 | 0.70 | Q | 81.10 | 62.50 |
| 2 | 1.00 | 1.00 | 0.27 | 0.73 | S | 85.13 | 37.50 |
| 4 | 1.00 | 1.00 | 0.60 | 0.85 | L | 92.00 | 75.00 |
| 7 | 1.00 | 1.00 | 0.77 | 0.99 | P | 99.32 | 87.50 |
| 11 | 0.59 | 0.52 | 0.53 | 0.51 | V | 59.88 | 37.50 |
| 14 | 0.59 | 0.52 | 0.49 | 0.51 | A | 59.95 | 31.25 |
| 46 | 1.00 | 1.00 | 0.70 | 0.80 | Q | 89.00 | 81.25 |
| 53 | 1.00 | 1.00 | 0.49 | 0.90 | K | 94.63 | 68.75 |
| 82 | 1.00 | 1.00 | 0.60 | 0.90 | K | 94.88 | 75.00 |
| 92 | 0.59 | 0.68 | 0.51 | 0.54 | A | 69.82 | 68.75 |
| 103 | 1.00 | 1.00 | 0.50 | 0.86 | D | 92.84 | 68.75 |

As set forth in Tables 3-8 above, it was found that a subset of residue positions in the QC system selected scFv frameworks were strongly biased towards certain residues not present or under-represented in the germlines (VBase and IMGT) and in mature antibodies (KDB), suggested that the stability of scFv can be rationally improved based on the unique features of the framework sequences selected in the Quality Control Yeast Screening System.

Example 4: Selection of Preferred Residues

In order to select preferred amino acid residue substitutions (or, alternatively, exclude amino acid residues) at a particular amino acid position known to improve the functional properties (e.g., stability and/or solubility) of a scFv, VH and VL sequences from the Kabat database of matured antibody sequences were grouped according to their family subtype (e.g., VH1b, VH3, etc.). Within each subfamily of sequences, the frequency of each amino acid residue at each amino acid position was determined as a percentage of all the analyzed sequences of one group of subtypes. The same was done for all the sequences of the QC database consisting of antibodies that were preselected for enhanced stability and/or solubility by the so-called QC system. For each subtype, the resulting percentages (relative frequencies) for each amino acid residue obtained for the Kabat sequences and for the QC sequences were compared at each corresponding position. In the event that the relative frequency of a certain amino acid residue was increased in the QC database relative to the Kabat database, the respective residue was considered a preferred residue at the given position to improve the stability and/or solubility of a scFv. Conversely, in the case that the relative frequency of a certain amino acid residue was decreased in the QC database as compared to the Kabat database, the respective residue was considered unfavorable at that position in the context of a scFv format.

Table 9 depicts an exemplary analysis of the residue frequency at amino acid position H78 (AHo numbering; Kabat position H67) for the VH1b subtype in the different databases. The columns in Table 9 are as follows: column 1: residue type; column 2: residue frequency in IMGT germline database; column 3: residue frequency in Vbase germline database; column 4: residue frequency in a QC database; column 5: residue frequency in a Kabat database.

TABLE 9

Relative residue frequency at position 78 (AHo numbering) for the VH1b subtype in two germline databases, a QC database, and a Kabat database of mature antibodies.

| Residue | IMGT_germ | Vbase_germ | QC database | KDB_VH1B |
|---|---|---|---|---|
| D | | | | |
| E | | | | |
| K | | | | |
| R | | | | |
| H | | | | |
| T | | | | |
| S | | | | |
| N | | | | |
| Q | | | | |
| G | | | | |
| A | | | 24 | 2 |
| C | | | | |
| P | | | | |
| V | 91 | 100 | 47 | 86 |
| I | | | 18 | 1 |
| L | | | 12 | |
| M | | | | |
| F | 9 | | | 10 |
| Y | | | | |
| W | | | | |
| Consensus | V | V | V | V |
| % Agree | 91 | 100 | 47 | 86 |
| # of Seq* | 11 | 11 | 17 | 81 |

*Number of sequences collected for the analysis of residue frequency

In the QC database, an alanine (A) residue was observed at a frequency of 24%, a factor of 12 above the 2% frequency observed for the same residue in a mature Kabat database (KDB_VH1B). Accordingly, an alanine residue at position H78 (AHo numbering) is considered a preferred residue at that position for enhancing the functional properties (e.g., stability and/or solubility) of a scFv. In contrast, a valine (V) residue was observed in the QC database at a relative frequency of 47%, much lower than the 86% frequency observed in the mature Kabat database and the more than 90% frequency observed for the same residue in germline databases (91% in IMGT-germ and 100% in Vbase germ). Therefore, a valine residue (V) was considered to be an unfavorable residue at position H78 in the context of an scFv format.

Example 5: Comparison of ESBA105 scFv Variants from Two Different Approaches In this example, the stability of scFv variants prepared by two different approaches was compared. The parental scFv antibody was ESBA 105, which has previously been described (see e.g., PCT Publications WO 2006/131013 and WO 2008/006235). One set of ESBA 105 variants was selected using the Quality Control Yeast Screening System ("QC variants"), which variants also have been previously described (see e.g., PCT Publications WO 2006/131013 and WO 2008/006235). The other set of variants was prepared by back-mutating certain amino acid positions to the preferred germline consensus sequence identified by the sequence analysis described in Examples 2 and 3 above. The back-mutations were selected by searching within the amino acid sequences for positions that were conserved in the germline sequence but that contained an unusual or low frequency amino acid in the selected scFv (referred to as the germline consensus engineering approach).

All of the variants were tested for stability by subjecting the molecules to a thermal induced stress. By challenging at a broad range of temperatures (25-95° C.) it was possible to determine approximate midpoints of the thermal unfolding transitions (TM) for every variant. Thermostability measurements for the wild type molecules and the variants were performed with the FT-IR ATR spectroscopy where the IR light was guided through an interferometer. The measured signal is the interferogram, performing a Fourier transformation on this signal the final spectrum is identical to that from conventional (dispersive) infrared spectroscopy.

Figure 6:
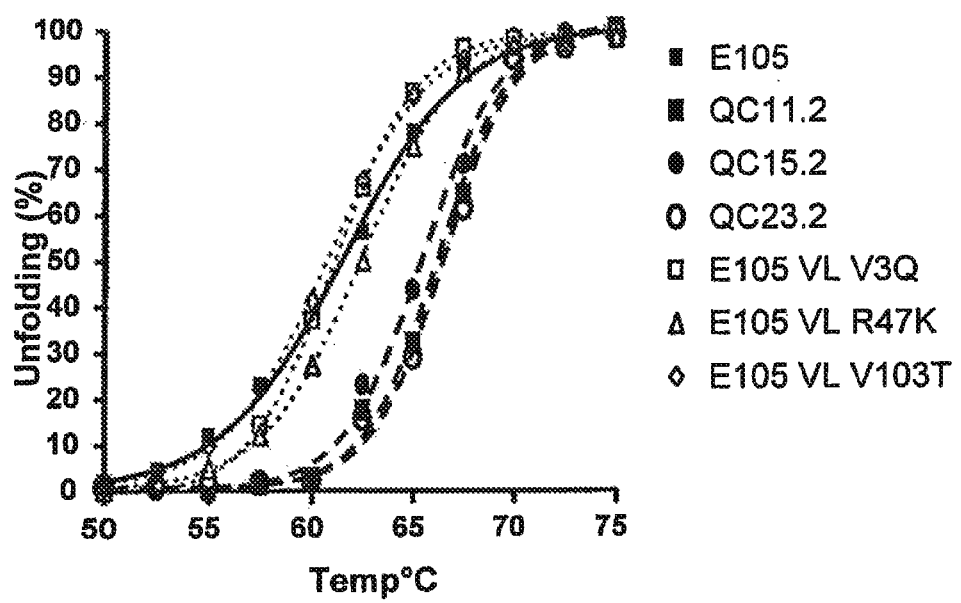
FIG. 6 depicts the denaturation profile observed for ESBA105 variants following thermo-induced stress at a range of temperatures from 25 to 95° C. ESBA-105 variants having backmutations to germline consensus residues (V3Q, R47K, or V103T) are indicated by dashed lines. Variants comprising preferred substitutions identified by the methods of the invention (QC11.2, QC15.2, and QC23.2) are indicated by solid lines.

The thermal unfolding results are summarized below in Table 10 and graphically depicted in FIG. 6. The columns in Table 10 are as follows: column 1: ESBA 105 variants; column 2: domain containing the mutation; column 3: mutation(s) in AHo numbering; column 4: TM midpoints calculated from the thermal unfolding curves in FIG. 6; column 5: relative activity compared to the parental ESBA 105; column 5: mutagenesis strategy for the variant specified in column 1.

TABLE 10

Comparison of ESBA105 variants from two different approaches and their contribution to overall stability measured in FT-IR (Midpoints calculated for the thermal unfolding transitions).

| Variant | Domain | Mutation | TM ° C. | Activity | Description |
|---|---|---|---|---|---|
| E105 | | | 61.53 | | Parental molecule |
| ESBA105_QC11.2 | VH | F78L | 66.26 | 1 | QC variant |
| ESBA105_QC15.2 | VH | K50R, F78I | 65.47 | 1 | QC variant |
| ESBA105_QC23.2 | VH | F78L | 66.53 | 1 | QC variant |
| ESBA105_VL R47K | VL | R47K | 62.4 | 0.9 | back-mutated to consensus |
| ESBA105_VL V103T | VL | V103T | 60.7 | 1 | back-mutated to consensus |
| ESBA105_VL V3Q | VL | V3Q | 61.9 | 1.2 | back-mutated to consensus |

As compared to the QC variants, the back mutations to the germline consensus had negative or no effect on the thermostability and activity of ESBA105. Thus, these results contradict the consensus engineering approach which has been used by others to improve stability in different antibodies and formats (see e.g., Steipe, B et al. (1994) *J. Mol. Biol.* 240:188-192; Ohage, E. and Steipe, B. (1999) *J. Mol. Biol.* 291:1119-1128; Knappik, A. et al. (2000) *J. Mol. Biol.* 296:57-86, Ewert, S. et al. (2003) Biochemistry 42:1517-1528; and Monsellier, E. and Bedouelle, H. (2006) *J. Mol. Biol.* 362:580-593).

Figure 7:
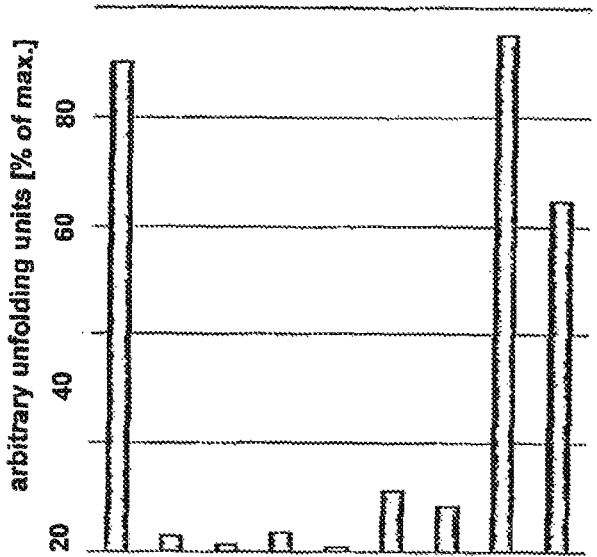
FIG. 7 depicts a comparison of the thermal stability for a set of ESBA105 variants comprising either consensus backmutations (S-2, D-2, D-3), a backmutation to alanine (D-1) or a QC residue (QC7.1, QC11.2, QC15.2, QC23.2). The identity of the framework residues at selected framework positions are provided in FIG. 7A. Residues which differ from the parental ESBA105 antibody are depicted in bold italics. Amino acid positions are provided in Kabat numbering. The thermal stability of each variant (in arbitrary unfolding units) is provided in FIG. 7B.

In a separate experiment, the above QC variants (QC11.2, QC15.2, and QC23.2) and an additional QC variant (QC7.1) were compared with a second set variants having either consensus backmutations (S-2, D-2, and D-3) or backmutation to alanine (D-1) (see FIG. 7). The identity of the residue at selected framework positions are indicated in FIG. 7A and the measured thermal stability (in arbitrary unfolding units) is depicted in FIG. 7B. Although some consensus variants (S-2 and D-1) exhibited a marked enhancement in thermal stability, this enhancement was less than the enhancement in thermal stability achieved by each of the four QC variants.

Accordingly, the results herein demonstrate that the selection pressure applied in the "Quality Control Yeast Screening System" yields a sub-population of scaffolds which do contain common features seldom observed in nature (yet still human) and presumably responsible for the superior biophysical properties of these frameworks. By challenging at 60° C. different variants of ESBA105, it was possible to reconfirm the superior properties of the preferred substitutions identified in the selected scFv framework database. Thus, the "functional consensus" approach described herein based on the selected scFv sequences obtained from the QC yeast screening system has been demonstrated to yield scFv variants having superior thermal stability than variants prepared using the germline consensus approach.

Example 6: ESBA212 scFv Variants

In this example, the stability of germline consensus variants of a scFv antibody (ESBA212) with a different binding specificity than ESBA105 were compared. All ESBA212 variants were prepared by back-mutating certain amino acid positions to the preferred germline consensus sequence identified by the sequence analysis described in Examples 2 and 3 above. The back-mutations were selected by searching within the amino acid sequences for positions that were conserved in the germline sequence but that contained an unusual or low frequency amino acid in the selected scFv (referred to as the germline consensus engineering approach). As in Example 5, all of the variants were tested for stability by subjecting the molecules to a thermal induced stress.

Figure 8:
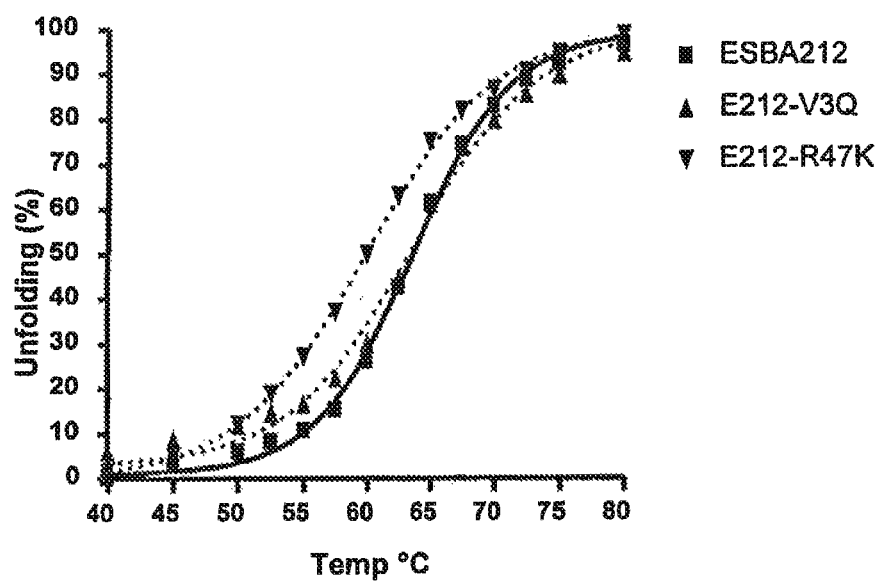
FIG. 8 depicts the denaturation profile observed for ESBA212 variants following thermo-induced stress at a range of temperatures from 25 to 95° C. ESBA-212 variants having backmutations to germline consensus residues (V3Q or R47K) are indicated by dashed lines. The parent ESBA212 molecule is indicated by a solid line.

The thermal unfolding results for the ESBA212 variants are summarized below in Table 11 and graphically depicted in FIG. 8. The columns in Table 11 are as follows: column 1: ESBA 212 variants; column 2: domain containing the mutation; column 3: mutation(s) in AHo numbering; column 4: TM midpoints calculated from the thermal unfolding curves in FIG. 7; column 5: relative activity compared to the parental ESBA 212; column 5: mutagenesis strategy for the variant specified in column 1.

TABLE 11

Comparison of ESBA212 variants back-mutated to the germline consensus residue and their contribution to overall stability measured in FT-IR (Midpoints calculated for the thermal unfolding transitions).

| Variant | Domain | Mutation | TM ° C. | Activity | Description |
|---|---|---|---|---|---|
| ESBA212 | | | 63.66 | | Parental molecule |
| ESBA212_VL R47K | VL | R47K | 59.94 | 2.8 | back-mutated to consensus |

TABLE 11-continued

Comparison of ESBA212 variants back-mutated to the germline consensus residue and their contribution to overall stability measured in FT-IR (Midpoints calculated for the thermal unfolding transitions).

| Variant | Domain | Mutation | TM °C. | Activity | Description |
|---|---|---|---|---|---|
| ESBA212_VL V3Q | VL | V3Q | 63.6 | 1.1 | back-mutated to consensus |

As observed for the unrelated ESBA105 scFv antibody, back mutations to the germline consensus had negative or no effect on the thermostability and activity of ESBA212. Thus, these results serve to further highlight the inadequacy of conventional consensus-based approaches. These deficiencies can be addressed by employing the functional consensus methodology of the invention.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method of identifying an amino acid position for mutation in a single chain antibody (scFv), the scFv having $V_H$ and $V_L$ amino acid sequences, the method comprising:
   a) entering the scFv VH, VL, or VH and VL amino acid sequences into a database of functionally-selected scFvs that comprises a multiplicity of antibody VH, VL, or VH and VL amino acid sequences such that the scFv VH, VL, or VH and VL amino acid sequences are aligned with the antibody VH, VL, or VH and VL amino acid sequences of the database, the database being stored on a computer;
   b) comparing an amino acid position within the scFv $V_H$ or $V_L$ amino acid sequence with a corresponding position within the antibody $V_H$ or $V_L$ amino acid sequences of the database;
   c) determining whether the amino acid position within the scFv $V_H$ or $V_L$ amino acid sequence is occupied by an amino acid residue that is conserved at the corresponding position within the antibody $V_H$ or $V_L$ amino acid sequences of the database; and
   d) identifying the amino acid position within the scFv $V_H$ or $V_L$ amino acid sequence as an amino acid position for mutation when the amino acid position is occupied by an amino acid residue that is not conserved at the corresponding position within the antibody $V_H$ or $V_L$ amino acid sequences of the database,
   the method further comprising mutating the amino acid position identified for mutation within the scFv $V_H$ or $V_L$ amino acid sequence, and wherein the amino acid position identified for mutation is mutated by random mutagenesis or by biased mutagenesis to generate a library of mutated scFvs, followed by screening of the library of mutated scFvs and selection of scFvs having at least one improved functional property.

2. The method of claim 1, wherein the library is screened using a yeast Quality Control-system (QC-system).

* * * * *